(12) United States Patent
Lowman et al.

(10) Patent No.: US 10,894,821 B2
(45) Date of Patent: Jan. 19, 2021

(54) ACTIVATABLE ANTIBODIES HAVING NON-BINDING STERIC MOIETIES AND METHODS OF USING THE SAME

(71) Applicant: CytomX Therapeutics, Inc., South San Francisco, CA (US)

(72) Inventors: Henry Bernard Lowman, El Granada, CA (US); Shouchun Liu, Burlingame, CA (US)

(73) Assignee: CytomX Therapeutics, Inc., South San Francisco, CA (US)

(*) Notice: Subject to any disclaimer, the term of this patent is extended or adjusted under 35 U.S.C. 154(b) by 0 days.

(21) Appl. No.: 15/840,528

(22) Filed: Dec. 13, 2017

(65) Prior Publication Data
US 2018/0298085 A1   Oct. 18, 2018

Related U.S. Application Data

(62) Division of application No. 13/924,207, filed on Jun. 21, 2013, now Pat. No. 9,856,314.

(60) Provisional application No. 61/663,151, filed on Jun. 22, 2012.

(51) Int. Cl.
| | |
|---|---|
| *C07K 16/28* | (2006.01) |
| *A61K 39/395* | (2006.01) |
| *A61K 47/68* | (2017.01) |
| *C07K 16/18* | (2006.01) |
| *G01N 33/574* | (2006.01) |
| *C07K 16/00* | (2006.01) |

(52) U.S. Cl.
CPC .............. *C07K 16/18* (2013.01); *C07K 16/00* (2013.01); *C07K 16/2863* (2013.01); *G01N 33/574* (2013.01); *C07K 2319/00* (2013.01)

(58) Field of Classification Search
CPC  C07K 16/2863; C07K 2319/00; C07K 16/18; C07K 2317/50; C07K 2317/54; C07K 2317/56; C07K 2317/565; C07K 2317/569; C07K 2317/622; C07K 2317/30; C07K 2317/52; C07K 2317/73; C07K 2317/76; C07K 2317/92; C07K 2317/21; A61K 39/39558; A61K 2039/505; A61K 48/0058; A61K 47/6849; A61K 47/6801; A61K 47/6805; A61K 47/6809; A61K 47/6811; A61P 35/00
See application file for complete search history.

(56) References Cited

U.S. PATENT DOCUMENTS

| | | | |
|---|---|---|---|
| 4,485,045 A | 11/1984 | Regen | |
| 4,544,545 A | 10/1985 | Ryan et al. | |
| 5,013,556 A | 5/1991 | Woodle et al. | |
| 5,030,719 A | 7/1991 | Umemoto et al. | |
| 7,341,720 B2 | 3/2008 | Stefano | |
| 7,465,790 B2 | 12/2008 | Waldmann et al. | |
| 7,608,681 B2 | 10/2009 | Dennis et al. | |
| 8,513,390 B2 | 8/2013 | Stagliano et al. | |
| 8,518,404 B2 | 8/2013 | Daugherty et al. | |
| 8,529,898 B2 | 9/2013 | Daugherty et al. | |
| 8,541,203 B2 | 9/2013 | Daugherty et al. | |
| 8,563,269 B2 | 10/2013 | Stagliano et al. | |
| 8,809,504 B2 | 8/2014 | Lauermann | |
| 9,169,321 B2 | 10/2015 | Daugherty et al. | |
| 9,453,078 B2 | 9/2016 | Stagliano et al. | |
| 9,856,314 B2* | 1/2018 | Lowman | C07K 16/00 |
| 10,059,762 B2 | 8/2018 | Stagliano et al. | |
| 10,118,961 B2 | 11/2018 | Stagliano et al. | |
| 2003/0069395 A1 | 4/2003 | Sato et al. | |
| 2004/0109855 A1 | 6/2004 | Waldmann et al. | |
| 2009/0304719 A1 | 12/2009 | Daugherty et al. | |
| 2010/0021460 A1 | 1/2010 | Deng et al. | |
| 2010/0189651 A1 | 7/2010 | Stagliano et al. | |
| 2012/0149061 A1 | 6/2012 | Stagliano et al. | |
| 2012/0207756 A1 | 8/2012 | Stagliano et al. | |
| 2012/0237512 A1 | 9/2012 | Stagliano et al. | |
| 2012/0237977 A1 | 9/2012 | Daugherty et al. | |
| 2012/0244154 A1 | 9/2012 | Daugherty et al. | |
| 2013/0060010 A1* | 3/2013 | Williams | C07K 16/2863 530/387.3 |
| 2013/0309230 A1 | 11/2013 | Stagliano et al. | |
| 2014/0024810 A1 | 1/2014 | Stagliano et al. | |
| 2014/0045195 A1 | 2/2014 | Daugherty et al. | |
| 2016/0122425 A1 | 5/2016 | Daugherty et al. | |
| 2016/0228546 A1 | 8/2016 | Stagliano et al. | |
| 2017/0081397 A1 | 3/2017 | Stagliano et al. | |
| 2019/0119370 A1 | 4/2019 | Stagliano et al. | |

FOREIGN PATENT DOCUMENTS

| | | |
|---|---|---|
| EP | 1 523 503 B1 | 4/2009 |
| EP | 1 324 771 B1 | 6/2011 |
| WO | WO 2001/91798 A2 | 12/2001 |
| WO | WO 2002/030460 A2 | 4/2002 |
| WO | WO 2004/009638 A1 | 1/2004 |

(Continued)

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Caldas et al. "Humanization of the anti-CD18 antibody 6.7: an unexpected effect of a framework residue in binding to antigen" *Mol Immunol* 39 (15): 941-952 (2003).
Delano et al. "Convergent solutions to binding at a protein-protein interface" *Science* 287(5456):1279-1283 (2000).

(Continued)

*Primary Examiner* — Phuong Huynh
(74) *Attorney, Agent, or Firm* — Cooley LLP; Ivor R Elrifi; Cynthia A. Kozakiewicz

(57) ABSTRACT

The invention relates generally to activatable antibodies and methods of making and using these activatable antibodies in a variety of therapeutic, diagnostic and prophylactic indications.

14 Claims, 3 Drawing Sheets
Specification includes a Sequence Listing.

(56) References Cited

FOREIGN PATENT DOCUMENTS

| WO | WO 2007/105027 A1 | 9/2007 |
|----|-------------------|--------|
| WO | WO 2009/025846 A2 | 2/2009 |
| WO | WO 2010/081173 A2 | 7/2010 |

OTHER PUBLICATIONS

Dennis et al. "Albumin Binding as a General Strategy for Improving the Pharmacokinetics of Proteins" *J. Biol. Chem.* 227: 35035-35043 (2002).

Dennis et al. "Engineering as a Means to Improve the Pharmacokinetics of Injected Therapeutic Proteins," in *Proteins and Peptides: Pharmacokinetic, Pharmacodynamic and Metabolic Outcomes*. R Mrsny and A Daugherty, eds., Informa Healthcare, New York, 2009.

Golay et al. "Mechanism of action of therapeutic monoclonal antibodies: promises and pitfalls of in vitro and in vivo assays" *Archives of Biochemistry and Biophysics*, 526:146-153 (2012).

Irving, B.A. (Feb. 2015) "Probodies Empower a New Generation of Antibody Immunotherapies," CytomX Therapeutics Inc. presentation at Keystone Symposia™ on Molecular and Cellular Biology, Feb. 8-13, 2015; 25 pages.

Janeway et al., *Immunobiology. The Immune System in Health and Disease*. Third Edition, Garland Publishing Inc., New York and London; pp. 3:1 to 3:11, 1994.

Nguyen, A et al. "The pharmacokinetics of an albumin-binding Fab (AB.Fab) can be modulated as a function of affinity for albumin" *Protein Eng Des Sel*. 19(7):291-7 (2006).

Rudikoff et al. "Single amino acid substitution altering antigen-binding specificity" *Proc Natl Acad Sci USA*, 79:1979-1983 (1982).

Stancovski et al. "Mechanistic aspects of the opposing effects of monoclonal antibodies to the ERBB2 receptor on tumor growth" *PNAS*, 88:8691-8695 (1991).

Wang et al. "Protease regulated antibodies" Abstract #227, Keystone Symposium. Antibodies as Drugs, Feb. 6-11, 2011.

Winkler et al. "Changing the antigen binding specificity by single point mutations of an anti-p24 (HIV-1) antibody" *J. Immunology*, 165:4505-4514 (2000).

Yu et al. "Interaction between bevacizumab and murine VEGF-A: a reassessment" *Investigative Ophthalmology & Visual Science*, 49(2):522-527 (2008).

\* cited by examiner

US 10,894,821 B2

ACTIVATABLE ANTIBODIES HAVING NON-BINDING STERIC MOIETIES AND METHODS OF USING THE SAME

RELATED APPLICATIONS

This application is a divisional of U.S. patent application Ser. No. 13/924,207, filed Jun. 21, 2013, now U.S. Pat. No. 9,856,314, issued Jan. 2, 2018, which claims the benefit of U.S. Provisional Patent Application No. 61/663,151, filed Jun. 22, 2012, the contents of which are incorporated herein by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: CYTM_018_DO1_US_SeqList_ST25.txt, date recorded: Jul. 2, 2018, file size 36.0 kilobytes).

FIELD OF THE INVENTION

The invention relates generally to activatable antibodies and methods of making and using these activatable antibodies in a variety of therapeutic, diagnostic and prophylactic indications.

BACKGROUND OF THE INVENTION

Antibody-based therapies have proven effective treatments for some diseases but in some cases, toxicities due to broad target expression have limited their therapeutic effectiveness. In addition, antibody-based therapeutics have exhibited other limitations such as rapid clearance from the circulation following administration.

In the realm of small molecule therapeutics, strategies have been developed to provide prodrugs of an active chemical entity. Such prodrugs are administered in a relatively inactive (or significantly less active) form. Once administered, the prodrug is metabolized in vivo into the active compound. Such prodrug strategies can provide for increased selectivity of the drug for its intended target and for a reduction of adverse effects.

Accordingly, there is a continued need in the field of antibody-based therapeutics for antibodies that mimic the desirable characteristics of the small molecule prodrug.

SUMMARY OF THE INVENTION

The invention provides activatable antibodies that include non-binding steric moieties (NB) or binding partners (BP) for non-binding steric moieties, where the BP recruits or otherwise attracts the NB to the activatable antibody. The activatable antibodies provided herein include, for example, an activatable antibody that includes a non-binding steric moiety (NB), a cleavable linker (CL) and antibody or antibody fragment (AB); an activatable antibody that includes a binding partner for a non-binding steric moiety (BP), a CL and an AB; and an activatable antibody that includes a BP to which an NB has been recruited, a CL and an AB. Activatable antibodies in which the NB is covalently linked to the CL and AB of the activatable antibody or is associated by interaction with a BP that is covalently linked to the CL and AB of the activatable antibody are referred to herein as "NB-containing activatable antibodies." By activatable or switchable is meant that the activatable antibody exhibits a first level of binding to a target when the activatable antibody is in an inhibited, masked or uncleaved state (i.e., a first conformation), and a second level of binding to the target when the activatable antibody is in an uninhibited, unmasked and/or cleaved state (i.e., a second conformation, i.e., activated antibody), where the second level of target binding is greater than the first level of target binding. The activatable antibody compositions can exhibit increased bioavailability and more favorable biodistribution compared to conventional antibody therapeutics.

The activatable antibodies of the invention include an activatable antibody that includes a non-binding steric moiety (NB) or a binding partner (BP) for a non-binding steric moiety, a cleavable linker (CL), and an antibody or antibody fragment (AB). In general, the access of target to the AB of the activatable antibody is greater in the presence of an agent that cleaves the CL than in the absence of such a cleaving agent. Thus, when the activatable antibody is in the uncleaved state, the AB is masked or otherwise inhibited from target binding (i.e., the first conformation is such that the AB cannot bind the target), and in the cleaved state the AB is unmasked or otherwise not inhibited to target binding. As used herein, the term cleaved or cleaved state refers to the condition of the activatable antibody following modification of the CL by a protease and/or reduction of a cysteine-cysteine disulfide bond of the CL, and/or photoactivation. The term uncleaved or uncleaved state, as used herein, refers to the condition of the activatable antibody in the absence of cleavage of the CL by a protease and/or in the absence reduction of a cysteine-cysteine disulfide bond of the CL, and/or in the absence of light.

In some embodiments, the AB binds a target selected from the group consisting of the targets listed in Table 1. In some embodiments, the CL includes a substrate (S) for an enzyme selected from the group consisting of the enzymes listed in Table 3.

In some embodiments, the CL and AB of the activatable antibody are selected so that the AB represents a binding moiety for a target of interest, and the CL includes a substrate (S) for a protease that is co-localized with the target at a site in a subject, for example, a treatment site and/or a diagnosis site. In some embodiments, the CL includes at least a first flexible portion (FP1), a substrate (S) and a second flexile portion (FP2). In some embodiments, the CL includes at least a first flexible portion (FP1) and a substrate (S). In some embodiments, the CL includes at least a second flexible portion (FP2) and a substrate (S). In some embodiments, activatable antibodies contain at least one protease-cleavable CL. The activatable antibody can alternatively or further include a photolabile substrate, activatable by a light source or a cysteine-cysteine disulfide bond, and in some embodiments include both kinds of CLs.

The activatable antibodies disclosed herein are useful, for example, where an active protease capable of cleaving a substrate in the CL is present at relatively higher levels in target-containing tissue of a site, for example diseased tissue where therapeutic treatment or diagnosis can be effected, than in tissue of non-treatment sites (for example in healthy tissue). The activatable antibodies disclosed herein also find particular use where, for example, a reducing agent capable of reducing a substrate in the CL is present at relatively higher levels in target-containing tissue of a treatment or diagnostic site than in tissue of non-treatment or non-diagnostic sites. The activatable antibodies disclosed herein also find particular use where, for example, a light source, for example, by way of laser, capable of photolysing a substrate in the CL, is introduced to a target-containing tissue of a treatment or diagnostic site.

In some embodiments, activatable antibodies provide for reduced toxicity and/or adverse side effects that could otherwise result from binding of the AB at non-treatment sites and/or non-diagnostic sites if the AB were not masked or otherwise inhibited from binding to such a site. Where the activatable antibody contains a CL that is cleavable by a reducing agent that facilitates reduction of a disulfide bond, the ABs of such activatable antibodies may be selected to exploit activation of an AB where a target of interest is present at a desired treatment site and/or desired diagnostic site characterized by elevated levels of a reducing agent, such that the environment is of a higher reduction potential than, for example, an environment of a non-treatment site and/or a non-diagnostic site.

Activatable antibodies of the invention include antibodies where the CL includes one or more amino acid sequences that provide for flexibility at one or more of the NB-CL junction, the BP-CL junction, the CL-AB junction, or both the CL-AB and NB-CL or BP-CL junction. For example, the AB, NM, BP, and/or CL may not contain a sufficient number of residues (e.g., Gly, Ser, Asp, Asn, especially Gly and Ser, particularly Gly) to provide the desired flexibility. As such, the switchable phenotype of such activatable antibodies would benefit from introduction of one or more amino acids to provide for one or more flexible portions of the CL.

In general, an activatable antibody is designed by selecting an AB of interest and constructing the remainder of the activatable antibody so that the NB provides for masking of the AB, thereby reducing binding of the AB to its target. Structural design criteria are taken into account to provide for this functional feature.

In one embodiment, the activatable antibody includes a non-binding steric moiety (NB); a cleavable linker (CL); and an antibody or antibody fragment (AB) that binds specifically to a target, wherein the NB is a polypeptide that does not bind specifically to the AB; the CL is a polypeptide that includes a substrate (S) for an enzyme; the CL is positioned in the activatable antibody such that in an uncleaved state, the NB interferes with binding of the AB to the target and in a cleaved state, the NB does not interfere with binding of the AB to the target; and the NB does not inhibit cleavage of the CL by the enzyme. As used herein and throughout, the term polypeptide refers to any polypeptide that includes at least two amino acid residues, including larger polypeptides, full-length proteins and fragments thereof, and the term polypeptide is not limited to single-chain polypeptides and can include multi-unit, e.g., multi-chain, polypeptides. In cases where the polypeptide is of a shorter length, for example, less than 50 amino acids total, the terms peptide and polypeptide are used interchangeably herein, and in cases where the polypeptide is of a longer length, for example, 50 amino acids or greater, the terms polypeptide and protein are used interchangeably herein.

In one embodiment, the activatable antibody includes a non-binding steric moiety (NB); a cleavable linker (CL); and an antibody or antibody fragment (AB) that binds specifically to a target, wherein (i) the NB includes a polypeptide that does not bind specifically to the AB; (ii) CL is a polypeptide of up to 50 amino acids in length that includes a substrate (S) for an enzyme; (iii) the CL is positioned in the activatable antibody such that in an uncleaved state, the NB interferes with binding of the AB to the target and in a cleaved state, the NB does not interfere with binding of the AB to the target; and (iv) the NB does not inhibit cleavage of the CL by the enzyme. For example, the CL has a length of up to 15 amino acids, a length of up to 20 amino acids, a length of up to 25 amino acids, a length of up to 30 amino acids, a length of up to 35 amino acids, a length of up to 40 amino acids, a length of up to 45 amino acids, a length of up to 50 amino acids, a length in the range of 10-50 amino acids, a length in the range of 15-50 amino acids, a length in the range of 20-50 amino acids, a length in the range of 25-50 amino acids, a length in the range of 30-50 amino acids, a length in the range of 35-50 amino acids, a length in the range of 40-50 amino acids, a length in the range of 45-50 amino acids, a length in the range of 10-40 amino acids, a length in the range of 15-40 amino acids, a length in the range of 20-40 amino acids, a length in the range of 25-40 amino acids, a length in the range of 30-40 amino acids, a length in the range of 35-40 amino acids, a length in the range of 10-30 amino acids, a length in the range of 15-30 amino acids, a length in the range of 20-30 amino acids, a length in the range of 25-30 amino acids, a length in the range of 10-20 amino acids, or a length in the range of 10-15 amino acids.

In one embodiment, the activatable antibody includes a non-binding steric moiety (NB); a cleavable linker (CL); and an antibody or antibody fragment (AB) that binds specifically to a target, wherein (i) the NB includes a polypeptide that does not bind specifically to the AB; (ii) the CL is a polypeptide that includes a substrate (S) for an enzyme; (iii) the CL is positioned in the activatable antibody such that in an uncleaved state, the NB interferes with binding of the AB to the target and in a cleaved state, the NB does not interfere with binding of the AB to the target; (iv) the NB does not inhibit cleavage of the CL by the enzyme; and (v) the activatable antibody in the uncleaved state has the structural arrangement from N-terminus to C-terminus as follows: NB-CL-AB or AB-CL-NB;

In one embodiment, the activatable antibody includes a non-binding steric moiety (NB); a cleavable linker (CL); and an antibody or antibody fragment (AB) that binds specifically to a target, wherein (i) the NB includes a polypeptide that does not bind specifically to the AB; (ii) the CL is a polypeptide that includes a substrate (S) for an enzyme; (iii) the CL is positioned in the activatable antibody such that in an uncleaved state, the NB interferes with binding of the AB to the target and in a cleaved state, the NB does not interfere with binding of the AB to the target, and wherein the NB in the uncleaved activatable antibody reduces the ability of the AB to bind the target by at least 50%, for example, by at least 60%, by at least 70%, by at least 75%, by at least 80%, by at least 85%, by at least 90%, by at least 95%, by at least 96%, by at least 97%, by at least 98%, by at least 99%, by at least 100% as compared to the ability of the cleaved AB to bind the target; and (iv) the NB does not inhibit cleavage of the CL by the enzyme. The reduction in the ability of the AB to bind the target is determined, for example, using an assay as described herein or an in vitro target displacement assay such as, for example, the assay described in PCT Publication Nos. WO 2009/025846 and WO 2010/081173.

In one embodiment, the activatable antibody includes a binding partner (BP) for a non-binding steric moiety (NB); a cleavable linker (CL); and an antibody or antibody fragment (AB) that binds specifically to a target, wherein the BP is a polypeptide that binds to the NB when exposed thereto; the NB does not bind specifically to the AB; the CL is a polypeptide that includes a substrate (S) for an enzyme; the CL is positioned in the activatable antibody such that in an uncleaved state in the presence of the NB, the NB interferes with binding of the AB to the target and in a cleaved state, the NB does not interfere with binding of the AB to the target and the BP does not interfere with binding of the AB to the target; and the NB and the BP do not inhibit cleavage of the CL by the enzyme. In some examples of this embodiment, the BP of the activatable antibody is optionally bound to the NB. In one embodiment, the NB is recruited by the BP of the activatable antibody in vivo. In some examples of any of these activatable antibody embodiments, the activatable antibody is formulated as a composition. In some of these embodiments, the composition also includes the NB, where the NB is co-formulated with the activatable antibody that includes the BP, the CL, and the AB. In some examples of this embodiment, the BP is selected from the group consisting of an albumin binding peptide, a fibrinogen binding peptide, a fibronectin binding peptide, a hemoglobin binding peptide, a transferrin binding peptide, an immunoglobulin domain binding peptide, and other serum protein binding peptides.

In some examples of any of these activatable antibody embodiments, the NB is a soluble, globular protein. In some examples of any of these activatable antibody embodiments, the NB is a protein that circulates in the bloodstream. In some examples of any of these activatable antibody embodiments, the NB is selected from the group consisting of albumin, fibrinogen, fibronectin, hemoglobin, transferrin, an immunoglobulin domain, and other serum proteins.

In some examples of any of these activatable antibody embodiments, the CL is a polypeptide that includes a substrate (S) for a protease. In some examples of any of these activatable antibody embodiments, the protease is co-localized with the target in a tissue, and the protease cleaves the CL in the activatable antibody when the activatable antibody is exposed to the protease. In some examples of any of these activatable antibody embodiments, the CL is a polypeptide of up to 50 amino acids in length. In some examples of any of these activatable antibody embodiments, the CL is a polypeptide that includes a substrate (S) having a length of up to 15 amino acids, e.g., 3 amino acids long, 4 amino acids long, 5 amino acids long, 6 amino acids long, 7 amino acids long, 8 amino acids long, 9 amino acids long, 10 amino acids long, 11 amino acids long, 12 amino acids long, 13 amino acids long, 14 amino acids long, or 15 amino acids long.

In some examples of any of these activatable antibody embodiments, the activatable antibody in the uncleaved state has the structural arrangement from N-terminus to C-terminus as follows: NB-CL-AB, AB-CL-NB, BP-CL-AB or AB-CL-BP. In embodiments where the activatable antibody includes a BP and the activatable antibody is in the presence of the corresponding NB, the activatable antibody in the uncleaved state has a structural arrangement from N-terminus to C-terminus as follows: NB:BP-CL-AB or AB-CL-BP:NB, where ":" represents an interaction, e.g., binding, between the NB and BP.

In some examples of any of these activatable antibody embodiments, the CL includes one or more amino acid sequences that provide for flexibility at one or more of the NB-CL junction, the BP-CL junction, the CL-AB junction, or both the CL-AB and NB-CL or BP-CL junction. In some embodiments, the CL includes an amino acid sequence that is a substrate for a protease, e.g., an extracellular protease. In some embodiments, the CL includes at least a first flexible portion (FP1), a substrate (S) and a second flexible portion (FP2). In some embodiments, the CL includes at least a first flexible portion (FP1) and a substrate (S). In some embodiments, the CL includes at least a second flexible portion (FP2) and a substrate (S). In other embodiments, the CL includes a cysteine-cysteine pair that forms a disulfide bond, which is cleaved by action of a reducing agent. In other embodiments the CL includes a substrate that is cleaved upon photolysis.

In some examples of any of these activatable antibody embodiments, the activatable antibody includes a CL that includes an amino acid sequence that is a substrate (S) for a protease, a flexible portion between the CL and the AB.

In some examples of any of these activatable antibody embodiments, the activatable antibody includes a CL, which includes a substrate (S), a first flexible portion (FP1), and a second flexible portion (FP2), and wherein the activatable antibody in the uncleaved state has the structural arrangement from N-terminus to C-terminus as follows: NB-FP1-S-FP2-AB, AB-FP2-S-FP1-NB, BP-FP1-S-FP2-AB, AB-FP2-S-FP1-BP, NB:BP-FP1-S-FP2-AB or AB-FP2-S-FP1-BP:NB. The two flexible portions of the CL need not be identical to each other. In some examples of any of these activatable antibody embodiments, each of FP1 and FP2 is a peptide of about 1 to 20 amino acids in length.

In some examples of any of these activatable antibody embodiments, at least one of FP1 or FP2 includes an amino acid sequence selected from the group consisting of $(GS)_n$, $(GGS)_n$, $(GSGGS)_n$ (SEQ ID NO: 5) and $(GGGS)_n$ (SEQ ID NO: 6), where n is an integer of at least one. In some examples of any of these activatable antibody embodiments, at least one of FP1 or FP2 includes an amino acid sequence selected from the group consisting of GGSG (SEQ ID NO: 7), GGSGG (SEQ ID NO: 8), GSGSG (SEQ ID NO: 9), GSGGG (SEQ ID NO: 10), GGGSG (SEQ ID NO: 11), or GSSSG (SEQ ID NO: 12).

In some examples of any of these activatable antibody embodiments, the AB is an antigen binding fragment selected from the group consisting of a Fab fragment, a F(ab')$_2$ fragment, a scFv, a scab, a dAb, a single domain heavy chain antibody, and a single domain light chain antibody. In some examples of any of these activatable antibody embodiments, the AB is or is derived from cetuximab, panitumumab, zalutumumab, mapatumumab, matuzumab, nimotuzumab, ICR62, mAb 528, CH806, MDX-447 or any antibody listed in Table 2. For example, the AB is or is derived from cetuximab.

In some examples of any of these activatable antibody embodiments, the activatable antibody also includes a second AB wherein the target for the second AB is a target selected from the group consisting of the targets listed in Table 1.

In some examples of any of these activatable antibody embodiments, the CL includes an amino acid sequence that is a substrate for an enzyme selected from the group consisting of the enzymes listed in Table 3. For example, the CL includes an amino acid sequence that is a substrate for an enzyme selected from the group consisting of uPA, legumain, MT-SP1, MMP-9, MMP-14 and TMPRSS4.

The dissociation constant (IQ) of the NB-containing activatable antibody toward the target is greater than the $K_d$ of the AB towards the target when it is not associated with the NB or NB:BP. The dissociation constant (IQ) of the NB-containing activatable antibody toward the target is greater than the $K_d$ of the parental AB towards the target. For example, the IQ of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-

100,000, 10,000-1,000,000, 10,000-10,000,000, 100,000-1,000,000, or 100,000-10,000,000 times greater than the $K_d$ of the AB when it is not associated with the NB or NB:BP or the $K_d$ of the parental AB towards the target. Conversely, the binding affinity of the NB-containing activatable antibody towards the target is lower than the binding affinity of the AB when it is not associated with the NB or NB:BP or lower than the binding affinity of the parental AB towards the target. For example, the binding affinity of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB when it is not associated with the NB or NB:BP or lower than the binding affinity of the parental AB towards the target.

When the NB-containing activatable antibody is in the presence of the target, specific binding of the AB to its target is reduced or inhibited, as compared to the specific binding of the AB when it is not associated with the NB or NB:BP. When the NB-containing activatable antibody is in the presence of the target, specific binding of the AB to its target is reduced or inhibited, as compared to the specific binding of the parental AB to the target. When compared to the binding of the AB not associated with an NB or NB:BP or the binding of the parental AB to the target, the ability of the NB-containing activatable antibody to bind the target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

When the NB-containing activatable antibody is in the presence of the target but not in the presence of a modifying agent (for example a protease, other enzyme, reduction agent, or light), specific binding of the AB to its target is reduced or inhibited, as compared to the specific binding of the AB when it is not associated with the NB or NB:BP. When the NB-containing activatable antibody is in the presence of the target but not in the presence of a modifying agent (for example a protease, other enzyme, reduction agent, or light), specific binding of the AB to its target is reduced or inhibited, as compared to the specific binding of the parental AB to the target. When compared to the binding of the AB not associated with an NB or NB:BP or the binding of the parental AB to the target, the ability of the NB-containing activatable antibody to bind the target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

In some examples of any of these activatable antibody embodiments, the activatable antibody includes an agent conjugated to the AB to produce an activatable antibody conjugate. In some embodiments of the activatable antibody conjugate, the agent is a therapeutic agent. In some embodiments, the agent is a diagnostic agent. In some embodiments, the agent is a detectable marker. In some embodiments of the activatable antibody conjugate, the agent is an antineoplastic agent. In some embodiments of the activatable antibody conjugate, the agent is a toxin or fragment thereof. In some embodiments of the activatable antibody conjugate, the agent is an agent selected from the group consisting of the agents listed in Table 4. In some embodiments of the activatable antibody conjugate, the agent is conjugated to the AB via a linker. In some embodiments of the activatable antibody conjugate, the linker is a cleavable linker.

In some embodiments, the activatable antibody in an uncleaved state comprises a spacer that is joined directly to the NB or BP and has in the uncleaved state the structural arrangement from N-terminus to C-terminus of spacer-NB-CL-AB or spacer-BP-CL-AB. In some embodiments, the spacer includes at least the amino acid sequence QGQSGQ (SEQ ID NO: 37).

In some embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the AB via a linker. In some embodiments, the linker is a cleavable linker. In some embodiments, the agent is an agent selected from the group listed in Table 4. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some embodiments, the AB of the activatable antibody naturally contains one or more disulfide bonds. In some embodiments, the AB can be engineered to include one or more disulfide bonds.

In some embodiments, the activatable antibody is monospecific. In some embodiments, the activatable antibody is multispecific, e.g., by way of non-limiting example, bispecific or trifunctional. In some embodiments, the activatable antibody is formulated as part of a pro-Bispecific T Cell Engager (BITE) molecule. In some embodiments, the activatable antibody is formulated as part of a pro-Chimeric Antigen Receptor (CAR) modified T cell or other engineered receptor.

The disclosure also provides compositions and methods that include an activatable antibody that includes an antibody or antibody fragment (AB) that specifically binds a target, where the AB is coupled to a non-binding steric moiety (NB) or a binding partner (BP) for a non-binding steric moiety that decreases the ability of the AB to bind its target. In some embodiments, the activatable antibody further includes a cleavable linker (CL) that includes a substrate for a protease. The compositions and methods provided herein enable the attachment of one or more agents to one or more cysteine residues in the AB without compromising the activity (e.g., the masking, activating or binding activity) of the activatable antibody. In some embodiments, the compositions and methods provided herein enable the attachment of one or more agents to one or more cysteine residues in the AB without reducing or otherwise disturbing one or more disulfide bonds within the NB or BP. The compositions and methods provided herein produce an activatable antibody that is conjugated to one or more agents, e.g., any of a variety of therapeutic, diagnostic and/or prophylactic agents, preferably without any of the agent(s) being conjugated to the NB or BP of the activatable antibody. The compositions and methods provided herein produce conjugated activatable antibodies in which the NB or BP retains the ability to effectively and efficiently mask the AB of the activatable antibody in an uncleaved state. The compositions and methods provided herein produce conjugated activatable antibodies in which the activatable antibody is still activated, i.e., cleaved, in the presence of a protease that can cleave the CL.

The activatable antibodies have at least one point of conjugation for an agent, but in the methods and compositions provided herein less than all possible points of conjugation are available for conjugation to an agent. In some embodiments, the one or more points of conjugation are sulfur atoms involved in disulfide bonds. In some embodiments, the one or more points of conjugation are sulfur atoms involved in interchain disulfide bonds. In some embodiments, the one or more points of conjugation are sulfur atoms involved in interchain sulfide bonds, but not sulfur atoms involved in intrachain disulfide bonds. In some embodiments, the one or more points of conjugation are sulfur atoms of cysteine or other amino acid residues containing a sulfur atom. Such residues may occur naturally in the antibody structure or may be incorporated into the antibody by site-directed mutagenesis, chemical conversion, or mis-incorporation of non-natural amino acids.

Also provided are methods of preparing a conjugate of an activatable antibody having one or more interchain disulfide bonds in the AB and one or more intrachain disulfide bonds in the NB or BP, and a drug reactive with free thiols is provided. The method generally includes partially reducing interchain disulfide bonds in the activatable antibody with a reducing agent, such as, for example, TCEP; and conjugating the drug reactive with free thiols to the partially reduced activatable antibody. As used herein, the term partial reduction refers to situations where an activatable antibody is contacted with a reducing agent and less than all disulfide bonds, e.g., less than all possible sites of conjugation are reduced. In some embodiments, less than 99%, 98%, 97%, 96%, 95%, 90%, 85%, 80%, 75%, 70%, 65%, 60%, 55%, 50%, 45%, 40%, 35%, 30%, 25%, 20%, 15%, 10% or less than 5% of all possible sites of conjugation are reduced.

In yet other embodiments, a method of reducing and conjugating an agent, e.g., a drug, to an activatable antibody resulting in selectivity in the placement of the agent is provided. The method generally includes partially reducing the activatable antibody with a reducing agent such that any conjugation sites in the masking moiety or other non-AB portion of the activatable antibody are not reduced, and conjugating the agent to interchain thiols in the AB. The conjugation site(s) are selected so as to allow desired placement of an agent to allow conjugation to occur at a desired site. The reducing agent is, for example, TCEP. The reduction reaction conditions such as, for example, the ratio of reducing agent to activatable antibody, the length of incubation, the temperature during the incubation, the pH of the reducing reaction solution, etc., are determined by identifying the conditions that produce a conjugated activatable antibody in which the NB or BP retains the ability to effectively and efficiently mask the AB of the activatable antibody in an uncleaved state. The ratio of reduction agent to activatable antibody will vary depending on the activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1.

In some embodiments, a method of reducing interchain disulfide bonds in the AB of an activatable antibody and conjugating an agent, e.g., a thiol-containing agent such as a drug, to the resulting interchain thiols to selectively locate agent(s) on the AB is provided. The method generally includes partially reducing the AB with a reducing agent to form at least two interchain thiols without forming all possible interchain thiols in the activatable antibody; and conjugating the agent to the interchain thiols of the partially reduced AB. For example, the AB of the activatable antibody is partially reduced for about 1 hour at about 37° C. at a desired ratio of reducing agent:activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1.

The thiol-containing reagent can be, for example, cysteine or N-acetyl cysteine. The reducing agent can be, for example, TCEP. In some embodiments, the reduced activatable antibody can be purified prior to conjugation, using for example, column chromatography, dialysis, or diafiltration. Alternatively, the reduced antibody is not purified after partial reduction and prior to conjugation.

The invention also provides partially reduced activatable antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to a target, a non-binding steric moiety (NB) or a binding partner (BP) for a non-binding steric moiety that inhibits the binding of the AB of the activatable antibody in an uncleaved state to the target, and a cleavable linker (CL) coupled to the AB, wherein the CL is a polypeptide that functions as a substrate for a protease. In some embodiments, one or more intrachain disulfide bond(s) of the activatable antibody is not disturbed by the reducing agent. In some embodiments, one or more intrachain disulfide bond(s) of the NB or BP within the activatable antibody is not disturbed by the reducing agent. In some embodiments, the activatable antibody in the uncleaved state has the structural arrangement from N-terminus to C-terminus as follows: NB-CL-AB, AB-CL-NB, BP-CL-AB, or AB-CL-BP. In some embodiments, reducing agent is TCEP.

The invention provides compositions and methods of using conjugated activatable antibodies in which the conjugated agent(s), e.g., one or more toxins, damages a nucleic acid. These nucleic acid-damaging agents are also referred to herein as anti-nucleic acid agents and/or anti-nucleic acid-damaging agents. These compositions and methods are useful in a variety of therapeutic, diagnostic and prophylactic indications. For example, these compositions and methods are useful in targeting and inhibiting Kras mutant tumors and/or tumor cells or otherwise ameliorating a symptom of a Kras mutant tumor.

In some embodiments, the nucleic acid-damaging agent is a DNA-damaging agent. These DNA-damaging agents are also referred to herein as DNA-damaging agents. Suitable DNA-damaging agents for use in the compositions and methods of the disclosure include, by way of non-limiting examples, DNA alkylators, DNA binders, DNA intercalators, DNA double-strand breakers, and/or other DNA cleavage and/or DNA strand scission agents.

In some embodiments, the DNA-damaging agent is a duocarmycin or a derivative thereof. In some embodiments, the DNA-damaging agent is selected from the group consisting of: Duocarmycin A, Duocarmycin B1, Duocarmycin B2, Duocarmycin C1, Duocarmycin C2, Duocarmycin D, Duocarmycin SA, CC-1065, Adozelesin, Bizelesin, and Carzelesin. In some embodiments, the DNA damaging agent is selected from the group consisting of an acridine orange, adriamycin, calicheamicin, cisplatin, ellipticine, oxaliplatin, pyrrolo-benzodiazepine (PBD), another benzodiazepine, or a derivative of any of these agents.

In some embodiments, the conjugated activatable antibody includes an antibody or antigen-binding fragment thereof (AB) that specifically binds to a target that has KRAS or BRAF in its signaling pathway. In some embodiments, the AB specifically binds to a receptor tyrosine kinase (RTK).

In some embodiments, the conjugated activatable antibody includes an antibody or antigen-binding fragment thereof (AB) that specifically binds epidermal growth factor receptor (EGFR). In some embodiments, the AB is or is derived from an anti-EGFR antibody selected from the group consisting of cetuximab, panitumumab, zalutumumab, matuzumab, nimotuzumab, ICR62, mAb 528, CH806, and MDX-447.

In some embodiments, the conjugated activatable antibody is used in methods of treating, preventing and/or delaying the onset or progression of, or alleviating a symptom of an indication, e.g., disease or disorder, associated with aberrant expression and/or activity of the target in a subject using a conjugated activatable antibody that in an activated state binds the target, particularly a conjugated activatable antibody that binds and neutralizes or otherwise inhibits at least one biological activity of the target. In some embodiments, the target is EGFR.

In some embodiments, the indication, e.g., disease or disorder, associated with aberrant expression and/or activity of the target is a cancer. In some embodiments, the cancer is a Kras wild-type tumor. In some embodiments, the Kras wild-type tumor is a colorectal Kras wild-type tumor. In some embodiments, the Kras wild-type tumor is a lung Kras wild-type tumor, such as a non-small cell lung tumor. In some embodiments, the Kras wild-type tumor is a head and neck Kras wild-type tumor. In some embodiments, the Kras wild-type tumor is a breast Kras wild-type tumor, e.g., triple-negative breast cancer. In some embodiments, the Kras wild-type tumor is a gastric Kras wild-type tumor. In some embodiments, the Kras wild-type tumor is a glioblastoma Kras wild-type tumor. In some embodiments, the Kras wild-type tumor is an esophageal Kras wild-type tumor. In some embodiments, the Kras wild-type tumor is an ovarian/endometrial Kras wild-type tumor. In some embodiments, the Kras wild-type tumor is a pancreatic Kras wild-type tumor. In some embodiments, the Kras wild-type tumor is a prostate Kras wild-type tumor. In some embodiments, the Kras wild-type tumor is a renal Kras wild-type tumor. In some embodiments, the Kras wild-type tumor is a sarcoma Kras wild-type tumor, e.g., osteosarcoma. In some embodiments, the Kras wild-type tumor is a skin Kras wild-type tumor, e.g., basal cell, melanoma, or squamous cell tumor. In some embodiments, the subject is suffering from a Kras wild-type tumor, where the Kras wild-type tumor is non-responsive, less responsive or has stopped responding to a therapy, e.g., an EGFR inhibitor therapy.

In some embodiments, the cancer is a Kras mutant tumor. In some embodiments, the Kras mutant tumor is a colorectal Kras mutant tumor. In some embodiments, the Kras mutant tumor is a lung Kras mutant tumor, such as a non-small cell lung tumor. In some embodiments, the Kras mutant tumor is a head and neck Kras mutant tumor. In some embodiments, the Kras mutant tumor is a breast Kras mutant tumor, e.g., triple-negative breast cancer. In some embodiments, the Kras mutant tumor is a gastric Kras mutant tumor. In some embodiments, the Kras mutant tumor is a glioblastoma Kras mutant tumor. In some embodiments, the Kras mutant tumor is an esophageal Kras mutant tumor. In some embodiments, the Kras mutant tumor is an ovarian/endometrial Kras mutant tumor. In some embodiments, the Kras mutant tumor is a pancreatic Kras mutant tumor. In some embodiments, the Kras mutant tumor is a prostate Kras mutant tumor. In some embodiments, the Kras mutant tumor is a renal Kras mutant tumor. In some embodiments, the Kras mutant tumor is a sarcoma Kras mutant tumor, e.g., osteosarcoma. In some embodiments, the Kras mutant tumor is a skin Kras mutant tumor, e.g., basal cell, melanoma, or squamous cell tumor. In some embodiments, the subject is suffering from a Kras mutant tumor, where the Kras mutant is non-responsive, less responsive or has stopped responding to a therapy, e.g., an EGFR inhibitor therapy.

In some examples of any of these activatable antibody embodiments, the activatable antibodies are dual-target binding activatable antibodies. Such dual target binding activatable antibodies contain two ABs, which may bind the same or different targets. In specific embodiments, dual-targeting activatable antibodies contain bispecific antibodies or antibody fragments.

Dual target binding activatable antibodies are designed so as to have a CL cleavable by a cleaving agent that is co-localized in a target tissue with one or both of the targets capable of binding to the ABs of the activatable antibodies. Dual target binding activatable antibodies with more than one AB to the same or different targets can be designed so as to have more than one CL, wherein the first CL is cleavable by a cleaving agent in a first target tissue and wherein the second CL is cleavable by a cleaving agent in a second target tissue, with one or more of the targets binding to the ABs of the activatable antibodies. In one embodiment, the first and second target tissues are spatially separated, for example, at different sites in the organism. In one embodiment, the first and second target tissues are the same tissue temporally separated, for example the same tissue at two different points in time, for example the first time point is when the tissue is an early stage tumor, and the second time point is when the tissue is a late stage tumor.

The invention also provides nucleic acid molecules encoding the activatable antibodies described herein. The invention also provides vectors that include these nucleic acids. The activatable antibodies described herein are produced by culturing a cell under conditions that lead to expression of the activatable antibody, wherein the cell includes these nucleic acid molecules and/or vectors.

The invention also provides methods of manufacturing activatable antibodies. In one embodiment, the method includes the steps of (a) culturing a cell that includes a nucleic acid construct that encodes the activatable antibody under conditions that lead to expression of the activatable antibody, wherein the activatable antibody includes (i) a non-binding steric moiety (NB); (ii) a cleavable linker (CL); and (iii) an antibody or an antigen binding fragment thereof (AB) that specifically binds a target, wherein (1) the NB does not bind specifically to the AB; (2) the CL is a polypeptide that includes a substrate (S) for an enzyme; (3) the CL is positioned in the activatable antibody such that in an uncleaved state, the NB interferes with binding of the AB to the target and in a cleaved state, the NB does not interfere with binding of the AB to the target; and (4) the NB does not inhibit cleavage of the CL by the enzyme; and (b) recovering the activatable antibody.

In another embodiment, the method includes the steps of (a) culturing a cell that includes a nucleic acid construct that encodes the activatable antibody under conditions that lead to expression of the activatable antibody, wherein the activatable antibody includes (i) a binding partner (BP) for a non-binding steric moiety (NB); (ii) a cleavable linker (CL); and (iii) an antibody or an antigen binding fragment thereof (AB) that specifically binds a target, wherein (1) the NB does not bind specifically to the AB; (2) the CL is a polypeptide that includes a substrate (S) for an enzyme; (3) the CL is positioned in the activatable antibody such that in an uncleaved state in the presence of the NB, the NB interferes with binding of the AB to the target and in a cleaved state, the NB does not interfere with binding of the AB to the target and the BP does not interfere with binding of the AB to the target; and (4) the NB and the BP do not inhibit cleavage of the CL by the enzyme; and (b) recovering the activatable antibody. In some examples of this embodiment, the BP of the activatable antibody is bound to the NB.

In some examples of any of these methods of manufacturing activatable antibodies, the NB is a soluble, globular protein. In some examples of any of these methods of manufacturing activatable antibodies, the NB is a protein that circulates in the bloodstream. In some examples of any of these methods of manufacturing activatable antibodies, the NB is selected from the group consisting of albumin, fibrinogen, fibronectin, hemoglobin, transferrin, an immunoglobulin domain, and other serum proteins.

In some examples of any of these methods of manufacturing activatable antibodies, the CL is a polypeptide that functions as a substrate for a protease. In some examples of any of these methods of manufacturing activatable antibodies, the protease is co-localized with the target in a tissue, and wherein the protease cleaves the CL in the activatable antibody when the activatable antibody is exposed to the protease. In some examples of any of these methods of manufacturing activatable antibodies, the CL is a polypeptide of up to 50 amino acids in length. In some examples of any of these activatable antibody embodiments, the CL is a polypeptide that includes a substrate (S) having a length of up to 15 amino acids, e.g., 3 amino acids long, 4 amino acids long, 5 amino acids long, 6 amino acids long, 7 amino acids long, 8 amino acids long, 9 amino acids long, 10 amino acids long, 11 amino acids long, 12 amino acids long, 13 amino acids long, 14 amino acids long, or 15 amino acids long.

In some examples of any of these methods of manufacturing activatable antibodies, the activatable antibody in the uncleaved state has the structural arrangement from N-terminus to C-terminus as follows: NB-CL-AB, AB-CL-NB, BP-CL-AB or AB-CL-BP.

In some examples of any of these methods of manufacturing activatable antibodies, the CL includes one or more amino acid sequences that provide for flexibility at one or more of the NB-CL junction, the BP-CL junction, the CL-AB junction, or both the CL-AB and NB-CL or BP-CL junction. In some embodiments, the CL includes an amino acid sequence that is a substrate for a protease, e.g., an extracellular protease. In some embodiments, the CL includes at least a first flexible portion (FP1), a substrate (S) and a second flexible portion (FP2). In some embodiments, the CL includes at least a first flexible portion (FP1) and a substrate (S). In some embodiments, the CL includes at least a second flexible portion (FP2) and a substrate (S). In other embodiments, the CL includes a cysteine-cysteine pair that forms a disulfide bond, which is cleaved by action of a reducing agent. In other embodiments the CL includes a substrate that is cleaved upon photolysis.

In some examples of any of these methods of manufacturing activatable antibodies, the activatable antibody includes a CL that includes a substrate (S), a first flexible portion (FP1), and a second flexible portion (FP2), and wherein the activatable antibody in the uncleaved state has the structural arrangement from N-terminus to C-terminus as follows: NB-FP1-S-FP2-AB, AB-FP2-S-FP1-NB, BP-FP1-S-FP2-AB or AB-FP2-S-FP1-BP. The two flexible portions need not be identical to each other. In some examples of any of these methods of manufacturing activatable antibodies, each of FP1 and FP2 is a peptide of about 1 to 20 amino acids in length.

In some examples of any of these methods of manufacturing activatable antibodies, at least one of FP1 or FP2 includes an amino acid sequence selected from the group consisting of $(GS)_n$, $(GGS)_n$, $(GSGGS)_n$ (SEQ ID NO: 5) and $(GGGS)_n$ (SEQ ID NO: 6), where n is an integer of at least one. In some examples of any of these methods of manufacturing activatable antibodies, at least one of FP1 or FP2 includes an amino acid sequence selected from the group consisting of GGSG (SEQ ID NO: 7), GGSGG (SEQ ID NO: 8), GSGSG (SEQ ID NO: 9), GSGGG (SEQ ID NO: 10), GGGSG (SEQ ID NO: 11), or GSSSG (SEQ ID NO: 12).

In some examples of any of these methods of manufacturing activatable antibodies, the AB is an antigen binding fragment selected from the group consisting of a Fab fragment, a F(ab')$_2$ fragment, a scFv, a scab, a dAb, a single domain heavy chain antibody, and a single domain light chain antibody. In some examples of any of these methods of manufacturing activatable antibodies, the AB is or is derived from cetuximab, panitumumab, zalutumumab, mapatumumab, matuzumab, nimotuzumab, ICR62, mAb 528, CH806, MDX-447 or any antibody listed in Table 2. For example, the AB is or is derived from cetuximab.

In some examples of any of these methods of manufacturing activatable antibodies, the activatable antibody also includes a second AB wherein the target for the second AB is a target selected from the group consisting of the targets listed in Table 1.

In some examples of any of these methods of manufacturing activatable antibodies, the CL includes an amino acid sequence that is a substrate for an enzyme selected from the group consisting of the enzymes listed in Table 3. For example, the CL includes an amino acid sequence that is a substrate for an enzyme selected from the group consisting of uPA, legumain, MT-SP1, MMP-9, MMP-14 and TMPRSS4.

In some examples of any of these methods of manufacturing activatable antibodies, the method includes step (c) of conjugating an agent to the AB to produce an activatable antibody conjugate. In some embodiments of the activatable antibody conjugate, the agent is a therapeutic agent. In some embodiments, the agent is a diagnostic agent. In some embodiments, the agent is a detectable marker. In some embodiments of the activatable antibody conjugate, the agent is an antineoplastic agent. In some embodiments of the activatable antibody conjugate, the agent is a toxin or fragment thereof. In some embodiments of the activatable antibody conjugate, the agent is an agent selected from the group consisting of the agents listed in Table 4. In some embodiments of the activatable antibody conjugate, the agent is conjugated to the AB via a linker. In some embodiments of the activatable antibody conjugate, the linker is a cleavable linker.

The invention also provides methods of using the activatable antibodies and activatable antibody conjugates in various therapeutic and/or diagnostic indications. For example, the activatable antibodies and activatable antibody conjugates are used in the treatment and/or diagnosis of a disease or disorder in a subject. For example, the activatable antibodies and activatable antibody conjugates are used in the treatment and/or diagnosis of cancer or other neoplastic condition in a subject. In some embodiments, the activatable antibodies and activatable antibody conjugates are used in the treatment and/or diagnosis of an inflammatory disease such as rheumatoid arthritis (RA). In some embodiments, the activatable antibodies and activatable antibody conjugates are used in the treatment and/or diagnosis of a fibrotic disease such as idiopathic pulmonary fibrosis (IPF).

The conjugated activatable antibody can be administered at any stage of the disease. In some embodiments, a conjugated activatable antibody can be administered to a patient suffering cancer of any stage, from early to metastatic. In some embodiments, a conjugated activatable antibody can be administered to a patient suffering from an inflammatory disorder and/or autoimmune disease of any stage, from early onset to an advanced stage. It is to be understood that the terms subject and patient are used interchangeably herein.

The conjugated activatable antibodies are also useful in other therapeutic indications and treatment regimens. For example, the conjugated activatable antibodies of the embodiments provided herein can be used in a treatment regimen that includes neoadjuvant therapy.

In some embodiments, a conjugated activatable antibody is administered in combination with one or more additional agents such as, by way of non-limiting example, a chemotherapeutic agent. In some embodiments, the conjugated activatable antibody and the additional agent(s) are formulated in a single composition. In some embodiments, the conjugated activatable antibody and the additional agent(s) are administered as two or more separate compositions. In some embodiments, the activatable antibody and the additional agent(s) are administered simultaneously. In some embodiments, the conjugated activatable antibody and the additional agent(s) are administered sequentially.

The invention also provides antibodies and antibody fragments that have been modified to include a non-binding steric moiety (NB), as well as methods of using a non-binding steric moiety (NB) to modulate the pharmacokinetic and/or pharmacodynamic profile of an antibody or antibody fragment.

In one embodiment, the modified antibody or modified antibody fragment includes (a) an antibody or antigen binding fragment of an antibody (AB) that specifically binds to a target and has been modified to include a non-binding steric moiety (NB), wherein the NB does not bind specifically to the AB; and the NB is positioned such that the NB interferes with binding of the AB to the target.

In another embodiment, the modified antibody or modified antibody fragment includes (a) an antibody or antigen binding fragment of an antibody (AB) that specifically binds to a target and has been modified to include a binding partner (BP) for a non-binding steric moiety (NB); wherein the BP binds to the NB when exposed thereto; the NB does not bind specifically to the AB; and the BP is positioned such that when the BP is bound to the NB, the NB interferes with binding of the AB to the target.

In these modified antibodies and modified antibody fragments, the NB is any molecule that interferes with binding of the AB to the target. For example, the NB is a natural or synthetic molecule including, by way of non-limiting example, polypeptides (including peptides and proteins), small molecules, polymers and the like.

In some embodiments, the AB is an antigen binding fragment selected from the group consisting of a Fab fragment, a F(ab')$_2$ fragment, a scFv, a scab, a dAb, a single domain heavy chain antibody, and a single domain light chain antibody.

In some embodiments, the modified antibody or modified antibody fragment also includes at least flexible portion, for example, a flexible peptide. In some embodiments, the flexible portion includes an amino acid sequence selected from the group consisting of (GS)$_n$, (GGS)$_n$, (GSGGS)$_n$ (SEQ ID NO: 5) and (GGGS)$_n$ (SEQ ID NO: 6), where n is an integer of at least one. In some embodiments, the flexible portion includes an amino acid sequence selected from the group consisting of GGSG (SEQ ID NO: 7), GGSGG (SEQ ID NO: 8), GSGSG (SEQ ID NO: 9), GSGGG (SEQ ID NO: 10), GGGSG (SEQ ID NO: 11), or GSSSG (SEQ ID NO: 12).

The invention also provides an activatable antibody that includes (a) a non-binding steric moiety (NB) or a binding partner (BP) that recruits an NB, (b) a cleavable linker (CL), and an antibody or antibody fragment (AB) in which the AB is typically of a size such that the NB (i) not only interferes with binding of the AB to the target in an uncleaved state and does not interfere with binding of the AB to the target in a cleaved state (ii) but also increases the in vivo half-life ($t_{1/2}$) of the activatable antibody. In some embodiments, the AB is an antibody fragment, such as a scFv. In some embodiments, such an activatable antibody has a long-half life prior to cleavage, but once activated by cleavage of the CL, the released AB has a shorter half-life so as to reduce toxicity of the released AB. In some embodiments the released AB exhibits enhanced penetrance at a diseased tissue (e.g., a disease treatment site and/or diagnostic site).

The invention also provides kits for use in methods of detecting presence or absence of a cleaving agent and a target of interest in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent and the target are present in the subject or biological sample and wherein no detectable level of activated activatable antibody in the subject or biological sample indicates that the cleaving agent, the target or both the cleaving agent and the target are and/or not sufficiently present in the subject or biological sample, such that target binding and/or protease cleavage of the activatable antibody cannot be detected in the subject or biological sample.

The invention also provides methods of detecting presence or absence of a cleaving agent in a subject or a sample by (i) contacting a subject or biological sample with an activatable antibody in the presence of the target, and (ii) measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a non-binding steric moiety (NB) or a binding partner (BP), a cleavable linker (CL) that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: NB-CL-AB, AB-CL-NB, BP-CL-AB, or AB-CL-BP; wherein the NB or BP of the activatable antibody in an uncleaved state interferes with specific binding of the AB to the target, and wherein the NB or BP of an activatable antibody in a cleaved (i.e., activated) state does not interfere or compete with specific binding of the AB to the target. In some embodiments, the activatable antibody is a conjugated activatable antibody. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments all antigen binding sites are masked. In some embodiments, the measuring step includes use of a secondary reagent comprising a detectable label.

The invention also provides kits for use in methods of detecting presence or absence of a cleaving agent in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CL, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample.

The invention provides methods of detecting presence or absence of a cleaving agent and the target in a subject or a sample by (i) contacting a subject or biological sample with an activatable antibody, wherein the activatable antibody includes a detectable label that is positioned on a portion of the activatable antibody that is released following cleavage of the CL and (ii) measuring a level of activated activatable antibody in the subject or biological sample, wherein a detectable level of activated activatable antibody in the subject or biological sample indicates that the cleaving agent, the target or both the cleaving agent and the target are and/or not sufficiently present in the subject or biological sample, such that target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a non-binding steric moiety (NB) or a binding partner (BP), a cleavable linker (CL) that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: NB-CL-AB, AB-CL-NB, BP-CL-AB, or AB-CL-BP; wherein the NB or BP of the activatable antibody in an uncleaved state interferes with specific binding of the AB to the target, and wherein the NB or BP of an activatable antibody in a cleaved (i.e., activated) state does not interfere or compete with specific binding of the AB to the target. In some embodiments, the activatable antibody is a conjugated activatable antibody. In some embodiments, the activatable antibody is a conjugated activatable antibody. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The invention also provides kits for use in methods of detecting presence or absence of a cleaving agent and a target of interest in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent, the target or both the cleaving agent and the target are and/or not sufficiently present in the subject or biological sample, such that target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

The invention also provides methods of detecting presence or absence of a cleaving agent in a subject or a sample by (i) contacting a subject or biological sample with an activatable antibody, wherein the activatable antibody includes a detectable label that is positioned on a portion of the activatable antibody that is released following cleavage of the CL; and (ii) measuring a level of detectable label in the subject or biological sample, wherein a detectable level of the detectable label in the subject or biological sample indicates that the cleaving agent is absent and/or not sufficiently present in the subject or biological sample at a detectable level, such that protease cleavage of the activatable antibody cannot be detected in the subject or biological sample, and wherein a reduced detectable level of the detectable label in the subject or biological sample indicates that the cleaving agent is present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a non-binding steric moiety (NB) or a binding partner (BP), a cleavable linker (CL) that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: NB-CL-AB, AB-CL-NB, BP-CL-AB, or AB-CL-BP; wherein the NB or BP of the activatable antibody in an uncleaved state interferes with specific binding of the AB to the target, and wherein the NB or BP of an activatable antibody in a cleaved (i.e., activated) state does not interfere or compete with specific binding of the AB to the target. In some embodiments, the activatable antibody is a conjugated activatable antibody. In some embodiments, the activatable antibody is a conjugated activatable antibody. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The invention also provides kits for use in methods of detecting presence or absence of a cleaving agent of interest in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CL, wherein a detectable level of the detectable label in the subject or biological sample indicates that the cleaving agent, the target, or both the cleaving agent and the target are and/or not sufficiently present in the subject or biological sample, such that target binding and/or protease cleavage of the activatable antibody cannot be detected in the subject or biological sample, and wherein a reduced detectable level of the detectable label in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

In some embodiments, a method or kit is used to identify or otherwise refine a patient population suitable for treatment with an activatable antibody and/or conjugated activatable antibody of the disclosure, followed by treatment by administering that activatable antibody and/or conjugated activatable antibody to a subject in need thereof. For example, patients that test positive for both the target and a protease that cleaves the substrate in the cleavable linker (CL) of the activatable antibody and/or conjugated activatable antibody being tested in these methods are identified as suitable candidates for treatment with such antibody and/or such a conjugated activatable antibody comprising such a CL, and the patient is then administered a therapeutically effective amount of the activatable antibody and/or conjugated activatable antibody that was tested. Likewise, patients that test negative for either or both of the target and the protease that cleaves the substrate in the CL in the activatable antibody being tested using these methods might be identified as suitable candidates for another form of therapy. In some embodiments, such patients can be tested with other antibody and/or conjugated activatable antibody until a suitable antibody and/or conjugated activatable antibody for treatment is identified (e.g., an activatable antibody and/or conjugated activatable antibody comprising a CL that is cleaved by the patient at the site of disease). In some embodiments, the patient is then administered a therapeutically effective amount of the activatable antibody and/or conjugated for which the patient tested positive.

DETAILED DESCRIPTION OF THE INVENTION

Figure 1:
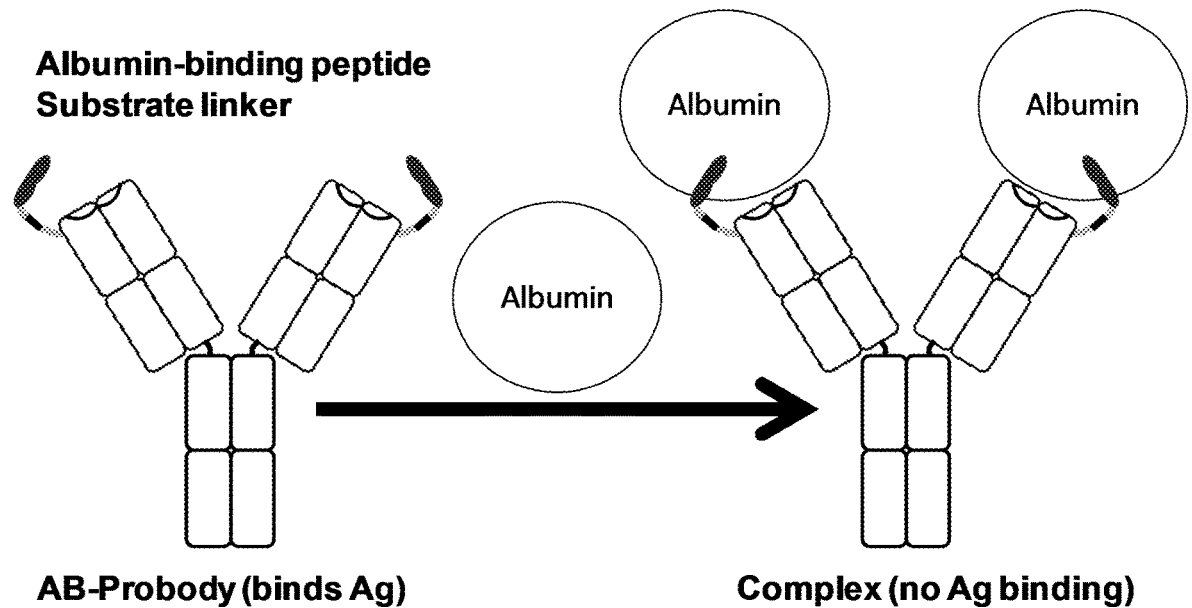
FIG. 1 is a schematic representation of one embodiment of an activatable antibody of the invention.

Activatable antibodies ("AA") that include a non-binding steric moiety are provided herein. Activatable antibodies in which the antigen-combining site ("ACS") of an antibody ("AB") is masked by a masking moiety ("MM") linked through a cleavable linker ("CL") to the antibody are described, for example, in PCT Publication No. WO 10/081173). Flexible peptide, "FP1" and "FP2," can be added to provide spacing for accessibility of the CL to cleaving enzymes, e.g., proteases. These constructs may have the form MM-FP1-CL-FP2-AB or AB-FP2-CL-FP1-MM. Upon cleavage of the CL, the MM is released, allowing the antibody to bind to the target antigen. The MM is covalently attached to the antibody and inhibits binding of the ACS to its target prior to cleavage of the CL.

The activatable antibodies of the instant invention include an activatable antibody that incorporates a non-binding steric moiety (abbreviated herein as "NB") that blocks the antigen-combining site of the antibody and is linked covalently to the antibody through a cleavable linker (CL). The NB blocks the AB in a manner other than by specifically binding to the AB. The NB, by virtue of its size and proximity to the antigen-combining site of the antibody, sterically blocks the approach of an antigen such as, for example, the binding partner of the AB. Activatable antibody constructs of the invention in the uncleaved state can have the structural arrangement or form: NB-CL-AB or AB-CL-NB. It should be noted that although NB and CL are indicated as distinct components in the formulae used herein, it is contemplated that the amino acid sequences of the NB and the CL could overlap, e.g., such that the CL is completely or partially contained within the NB. In addition, the formulae above provide for additional amino acid sequences that may be positioned N-terminal or C-terminal to the activatable antibody elements.

The NB can be incorporated into the activatable antibody in at least the following ways: (i) the NB can be covalently bound to the CL and AB; or (ii) a binding partner (BP) for the NB can be covalently joined to CL and AB, e.g., as BP-CL-AB or AB-CL-BP. The BP is a peptide or other combining partner for the NB. The constructs could potentially incorporate many different types of non-binding masking moieties, such as polyethylene glycol polymers, or functional proteins such as protein toxins or other bioactive agents.

The NB may be any protein that is of sufficient molecular size to provide steric blockade of the antigen-combining site of an antibody when fused to a site near the antigen-combining site. The fusion protein that includes an NB and an AB must also be readily synthesized (or expressed) and must be soluble under physiological conditions. Examples of potential NB moieties include serum albumin, transferrin, and immunoglobulin domains. Numerous protein fusions, including albumin fusions have been described in the literature as reviewed by Dennis, Yeung, Kelley & Lowman ("Engineering as a Means to Improve the Pharmacokinetics of Injected Therapeutic Proteins," in Proteins and Peptides: Pharmacokinetic, Pharmacodynamic and Metabolic Outcomes, R Mrsny and A Daugherty, eds., Informa Healthcare, New York, 2009). Light and co-workers have described a bispecific antibody construct consisting of a fusion protein of antibody fragments wherein the binding of one fragment to antigen may be blocked by the presence of a second antibody fragment fused at the N-terminus of the first (Wang et al., "Protease regulated antibodies," Abstract #227, Keystone Symposium: Antibodies as Drugs, Feb. 6-11, 2011).

A BP can be a peptide that is able to bind to the NB with sufficiently high affinity, such that in the bound state, the antibody is inhibited in its binding to antigen. In the case of constructs that include a BP, the BP does not provide the masking function itself; instead, it recruits interaction with the NB, which in turn provides the masking function. The NB may be provided by co-formulation with the BP-containing activatable antibody, or the NB may be provided from an endogenous source, for example, in the circulation of a patient or animal treated with the BP-containing activatable antibody.

Dennis et al. (J. Biol. Chem. 277, 35035, 2002) described albumin-binding peptides that can be used to extend the pharmacokinetic half-life of small molecules or proteins without interfering with the "active site" or antigen-combining site of the rapidly cleared molecule. For example, such peptides have been used to extend the half-life of the Fab fragment of an antibody by fusing the peptide at the C-terminus of a Fab—a location distal from the antigen-combining site of the antibody, to extend the Fab's half-life in animals (Nguyen et al., PEDS 19, 291, 2006; see also U.S. Pat. Nos. 7,608,681 and 7,635,749). IgG-Fc binding peptides have also been similarly described (DeLano et al., Science 287, 1279, 2000), however, these were not used in the masking context (i.e., the IgG-Fc binding peptides were not used to mask the ACS of an AB).

Activatable antibodies of the invention may be made biosynthetically using recombinant DNA technology and expression in eukaryotic or prokaryotic species. The cDNAs encoding the masking moiety, linker sequence (which may include a cleavable linker (CL), and antibody chain (heavy or light) can be linked in an 5' to 3' (N- to C-terminal in the translated product) sequence to create the nucleic acid construct, which is expressed as the activatable antibody protein following a conventional antibody expression process. Alternatively, the activatable antibody could be semi-synthetically produced by expressing a CL-antibody and then coupling the mask chemically at or near the N-terminus of the protein.

The activatable antibodies of the invention include an antibody or antibody fragment (collectively referred to as ABs). The ABs are directed against any antigen or hapten or determinant, e.g., tumor, bacterial, fungal, viral, parasitic, mycoplasmal, histocompatibility, differentiation and other cell membrane antigens, pathogen surface antigens, toxins, enzymes, allergens, drugs, intracellular targets, or any biologically active molecules. Additionally, a combination of ABs reactive to different antigenic determinants may be used.

As used herein, the AB is a full length antibody or an antibody fragment containing an antigen binding domain, which specifically binds to a target of interest, usually a protein target of interest. The AB is or is derived from, by way of non-limiting example, variable or hypervariable regions of light and/or heavy chains of an antibody ($V_L$, $V_H$), variable fragments (Fv), F(ab')$_2$ fragments, Fab fragments, single chain antibodies (scAb), single chain variable regions (scFv), complementarity determining regions (CDR), domain antibodies (dAbs), single domain heavy chain immunoglobulins of the BHH or BNAR type, single domain light chain immunoglobulins, or other polypeptides known in the art containing an AB capable of binding target proteins or epitopes on target proteins. In further embodiments, the AB is a chimera or hybrid combination containing more than one AB, for example a first AB and a second AB such that each AB binds to the same or different target. In some embodiments, the AB is a bispecific antibody or fragment thereof, designed to bind two different antigens. In some embodiments, the AB is a multispecific antibody or fragment thereof, designed to bind at least two or more antigens; the antigens can be the same or different antigens or a combination thereof.

The origin of the AB is, for example, a naturally occurring antibody or fragment thereof, a non-naturally occurring antibody or fragment thereof, a synthetic antibody or fragment thereof, a hybrid antibody or fragment thereof, or an engineered antibody or fragment thereof. The antibody can be a humanized antibody or fragment thereof.

Exemplary classes of targets of an AB include, but are not necessarily limited to, cell surface receptors and secreted binding proteins (e.g., growth factors), soluble enzymes, structural proteins (e.g. collagen, fibronectin) and the like. In some embodiments, activatable antibodies have an AB that binds an extracellular target, usually an extracellular protein target. In other embodiments, activatable antibodies are designed for cellular uptake and are switchable inside a cell.

As a non-limiting example, the AB is a binding partner for any target listed in Table 1.

As a nonlimiting example, the AB is or is derived from an antibody listed in Table 2.

TABLE 2

Exemplary sources for ABs

| Antibody Trade Name (antibody name) | Target |
|---|---|
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Ocerlizumab | CD20 |
| Arzerra ™ (ofatumumab) | CD20 |
| Zenapax ™ (daclizumab) | CD25 |

TABLE 1

Exemplary Targets

| | | | | | |
|---|---|---|---|---|---|
| 1-92-LFA-3 | CD117 | ERBB3 | IGF1R | MUC1 | TLR4 |
| Anti-Lewis-Y | CD132 (IL-2RG) | F protein of RSV | IL1B | Mucin-16 | TLR6 |
| Apelin J receptor | CD133 | FAP | IL1R | Na/K ATPase | TLR7 |
| APRIL | CD137 | FGF-2 | IL2 | Neutrophil elastase | TLR8 |
| BAFF | CD138 | FGF8 | IL11 | NGF | TLR9 |
| C5 complement | CD172A | FGFR1 | IL12 | Nicastrin | TNFalpha |
| C-242 | CEACAM5 (CEA) | FGFR2 | IL12p40 | Notch Receptors | TNFR |
| CD2 | CEACAM6 (NCA-90) | FGFR3 | IL-12R, IL-12Rbeta1 | Notch 1 | TRAIL-R1 |
| CD3 | CLAUDIN-3 | FGFR4 | IL13 | Notch 2 | TRAIL-R2 |
| CD9 | CLAUDIN-4 | Folate receptor | IL13R | Notch 3 | Transferrin |
| CD11a | cMet | G-CSF | IL15 | Notch 4 | Transferrin receptor |
| CD19 | Collagen | G-CSFR | IL17 | NOV | TRK-A |
| CD20 | Cripto | GLUT1 | IL18 | OSM-R | TRK-B |
| CD22 | CSFR | GLUT4 | IL21 | PAR2 | uPAR |
| CD25 | CSFR-1 | GM-CSF | IL23 | PDGF-AA | VCAM-1 |
| CD28 | CTLA-4 | GM-CSFR | IL23R | PDGF-BB | VEGF |
| CD30 | CTGF | GP IIb/IIIa receptors | IL27/IL27R (wsx1) | PDGFralpha | VEGF-A |
| CD33 | CXCL10 | Gp130 | IL29 | PDGFRbeta | VEGF-B |
| CD40 | CXCL13 | GPIIB/IIIA | IL-31R | PD-1 | VEGF-C |
| CD40L | CXCR1 | GPNMB | IL31/IL31R | PD-L1, PD-L2 | VEGF-D |
| CD41 | CXCR2 | HER2/neu | IL2R | Phosphatidyl-serine | VEGFR1 |
| CD44 | CXCR4 | HGF | IL4 | P1GF | VEGFR2 |
| CD47 | CYR61 | hGH | IL4R | PSCA | VEGFR3 |
| CD52 | DL44 | Hyaluronidase | IL6, IL6R | PSMA | WISP-1 |
| CD56 | DLL4 | IFNalpha | Insulin Receptor | RAAG12 | WISP-2 |
| CD64 | DPP-4 | IFNbeta | Jagged Ligands | RAGE | WISP-3 |
| CD70 | EGFR | IFNgamma | Jagged 1 | SLC44A4 | Alpha-4 integrin |
| CD80 | Endothelin B receptor (ETBR) | IgE | Jagged 2 | Sphingosine 1 Phosphate | Alpha-V integrin |
| CD86 | EpCAM | IgE Receptor (FceRI) | LIF-R | TGFbeta | alpha4beta1 integrin |
| CD95 | EPHA2 | IGF | MRP4 | TLR2 | alpha4beta7 integrin |

TABLE 2-continued

Exemplary sources for ABs

| Antibody Trade Name (antibody name) | Target |
|---|---|
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abciximab) | Glycoprotein receptor IIb/IIIa |
| Xolair ™ (omalizumab) | IgE |
| Herceptin ™ (trastuzumab) | Her2 |
| Synagis ™ (palivizumab) | F protein of RSV |
| (ipilimumab) | CTLA-4 |
| (tremelimumab) | CTLA-4 |
| Hu5c8 | CD40L |
| (pertuzumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |
| (mapatumumab) | EGFR |
| (matuzumab) | EGFR |
| (nimotuzumab) | EGFR |
| ICR62 | EGFR |
| mAb 528 | EGFR |
| CH806 | EGFR |
| MDX-447 | EGFR/CD64 |
| (edrecolomab) | EpCAM |
| RAV12 | RAAG12 |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta |
|  | Notch, e.g., Notch 1 Jagged 1 or Jagged 2 |
| (adecatumumab) | EpCAM |
| (figitumumab) | IGF1R |
| (tocilizumab) | IL-6 receptor |
| Stelara ™ (ustekinumab) | IL-12/IL-23 |
| Prolia ™ (denosumab) | RANKL |

In some embodiments, the AB is or is derived from cetuximab, panitumumab, zalutumumab, mapatumumab, matuzumab, nimotuzumab, ICR62, mAb 528, CH806, or MDX-447. For example, the AB is or is derived from cetuximab.

In some embodiments, the cleavable linker (CL) of the activatable antibody includes an amino acid sequence that is a substrate for a protease, usually an extracellular protease. In some embodiments, the CL includes at least a first flexible portion (FP1), a substrate (S) and a second flexible portion (FP2). In some embodiments, the CL includes at least a first flexible portion (FP1) and a substrate (S). In some embodiments, the CL includes at least a second flexible portion (FP2) and a substrate (S). In other embodiments, the CL includes a cysteine-cysteine pair that forms a disulfide bond, which is cleaved by action of a reducing agent. In other embodiments the CL includes a substrate that is cleaved upon photolysis.

The CL is positioned in the activatable antibody such that when the CL is cleaved by a cleaving agent (e.g., a protease substrate of a CL is cleaved by the protease and/or a cysteine-cysteine disulfide bond is disrupted via reduction by exposure to a reducing agent and/or cleavage occurs by light-induced photolysis) in the presence of a target, resulting in a cleaved state, the AB binds the target, and in an uncleaved state, in the presence of the target, binding of the AB to the target is inhibited by the NB.

The CL can have any length that allows the NB to have access to the AB, either directly or through interaction with the BP and to efficiently block AB binding to the target, but does not allow the NB to interfere or otherwise inhibit cleavage of the substrate (S) within the CL. For example, in some embodiments, the CL has a length of up to 50 amino acids, a length in the range of 10-50 amino acids, a length in the range of 15-50 amino acids, a length in the range of 20-50 amino acids, a length in the range of 25-50 amino acids, a length in the range of 30-50 amino acids, a length in the range of 35-50 amino acids, a length in the range of 40-50 amino acids, a length in the range of 45-50 amino acids, a length in the range of 10-40 amino acids, a length in the range of 15-40 amino acids, a length in the range of 20-40 amino acids, a length in the range of 25-40 amino acids, a length in the range of 30-40 amino acids, a length in the range of 35-40 amino acids, a length in the range of 10-30 amino acids, a length in the range of 15-30 amino acids, a length in the range of 20-30 amino acids, a length in the range of 25-30 amino acids, a length in the range of 10-20 amino acids, or a length in the range of 15-20 amino acids.

In some activatable antibodies, the CL is selected based on a protease that is co-localized in tissue with the desired target of the AB of the activatable antibody. A variety of different conditions are known in which a target of interest is co-localized with a protease, where the substrate of the protease is known in the art. In the example of cancer, the target tissue can be a cancerous tissue, particularly cancerous tissue of a solid tumor. Non-liming examples of disease include: all types of cancers (breast, lung, colorectal, prostate, head and neck, pancreatic, etc.), rheumatoid arthritis, Crohn's disease, melanomas, SLE, cardiovascular damage, ischemia, etc. Furthermore, anti-angiogenic targets, such as VEGF, are known. As such, where the AB of an AA is selected such that it is capable of binding an anti-angiogenic target such as VEGF, a suitable CL will be one which includes a peptide substrate that is cleaved by a protease that is present at the cancerous treatment site and/or diagnostic site, particularly one that is present at elevated levels at the cancerous treatment site and/or diagnostic site as compared to non-cancerous tissues. In other embodiments, the activatable antibody is activated by other disease-specific proteases, in diseases other than cancer such as inflammatory diseases or fibrosis.

The unmodified or uncleaved CL allows for efficient inhibition or masking of the AB by tethering the NB or NB:BP to the AB. When the CL is modified (cleaved, reduced, photolysed), the AB is no longer inhibited, i.e., it is unmasked and free to bind its target.

In some embodiments, the activatable antibody includes more than one substrate (S), for example, a first substrate (S1) and a second substrate (S2). For example, the S1 and S2 include amino acid sequences that are different substrates for the same enzyme (for example exhibiting different binding affinities to the enzyme), or amino acid sequences that are different substrates for different enzymes, or S1 includes an amino acid sequence that is an enzyme substrate and S2 includes an amino acid sequence that is be a photolysis substrate, or S1 includes an amino acid sequence that is an enzyme substrate and S2 includes an amino acid sequence that is a substrate for reduction, or S1 includes an amino acid sequence that is a substrate for photolysis and S2 includes an amino acid sequence that is a substrate for reduction, and the like.

By way of non-limiting example, the CL includes an amino acid sequence that is a substrate or is derived from a substrate that is cleaved by one or more of the following enzymes or proteases listed in Table 3.

By way of non-limiting example, the CL includes an amino acid sequence that is a substrate or is derived from a substrate that is cleaved by one or more of the following enzymes or proteases listed in Table 3.

TABLE 3

Exemplary Enzymes/Proteases

| | | |
|---|---|---|
| ADAMS, | Cathepsin S | MMP-15 |
| ADAMTS, e.g., | Cathepsin V/L2 | MMP-19 |
| ADAM8 | Cathepsin X/Z/P | MMP-23 |
| ADAM9 | | MMP-24 |
| ADAM10 | | MMP-26 |
| ADAM12 | Cysteine | MMP-27 |
| ADAM15 | proteinases, e.g., | |
| ADAM17/TACE | Cruzipain | |
| ADAMTS1 | Legumain | |
| ADAMTS4 | | Serine proteases, e.g., |
| ADAMTS5 | | activated protein C |
| | | Cathepsin A |
| | KLKs, e.g., | Cathepsin G |
| | KLK4 | Chymase |
| | KLK5 | coagulation factor proteases |
| Aspartate | | (e.g., FVIIa, FIXa, FXa, FXIa, |
| proteases, e.g., | | FXIIa) |
| | | Elastase |
| BACE | KLK6 | Granzyme B |
| | KLK7 | Guanidinobenzoatase |
| | KLK8 | Human Neutrophil Elastase |
| Aspartic | KLK10 | NS3/4A |
| cathepsins, e.g., | KLK11 | Plasmin |
| Cathepsin D | KLK13 | PSA |
| Cathepsin E | KLK14 | tPA |
| | | Thrombin |
| | | Tryptase |
| Caspases, e.g., | | uPA |
| Caspase 1 | Metallo | |
| Caspase 2 | proteinases, e.g., | |
| Caspase 3 | Meprin | |
| Caspase 4 | Neprilysin | Type II Transmembrane |
| Caspase 5 | PSMA | Serine Proteases (TTSPs), e.g., |
| Caspase 6 | BMP-1 | DESC1 |
| Caspase 7 | | DPP-4 |
| Caspase 8 | MMPs, e.g., | FAP |
| Caspase 9 | MMP-1 | Hepsin |
| Caspase 10 | MMP-2 | Matriptase-2 |
| Caspase 14 | MMP-3 | MT-SP1/Matriptase |
| | MMP-7 | TMPRSS2 |
| | MMP-8 | TMPRSS3 |
| | MMP-9 | TMPRSS4 |
| Cysteine | MMP-10 | |
| cathepsins, e.g., | MMP-11 | |
| Cathepsin B | MMP-12 | |
| Cathepsin C | MMP-13 | |
| Cathepsin K | MMP-14 | |
| Cathepsin L | | |

For example, the CL includes an amino acid sequence that is a substrate for an enzyme selected from the group consisting of uPA, legumain, MT-SP1, MMP-9, MMP-14, and TMPRSS4. In some embodiments, the CL includes an amino acid sequence that is a substrate for an enzyme selected from the group consisting of uPA, legumain, and MT-SP1. In some embodiments the CL includes an amino acid sequence that is a substrate for uPA. In some embodiments the CL includes an amino acid sequence that is a substrate for legumain. In some embodiments the CL includes an amino acid sequence that is a substrate for MT-SP1. In some embodiments the CL includes an amino acid sequence that is a substrate for MMP-9. In some embodiments the CL includes an amino acid sequence that is a substrate for MMP-14. In some embodiments the CL includes an amino acid sequence that is a substrate for TMPRSS4.

In embodiments where the CL includes an amino acid sequence that is a substrate for at least uPA, legumain and/or matriptase (MT-SP1), the substrate can include an amino acid sequence or can be derived from an amino acid sequence such as, for example TGRGPSWV (SEQ ID NO: 3, also referred to herein as 1203); SARGPSRW (SEQ ID NO: 22, also referred to herein as 1206); TARGPSFK (SEQ ID NO: 23, also referred to herein as 1216), TARGPSW (SEQ ID NO: 24, also referred to herein as Consensus 1), LSGRSDNH (SEQ ID NO: 25, also referred to herein as 1204), GGWHTGRN (SEQ ID NO: 26, also referred to herein as 1208), HTGRSGAL (SEQ ID NO: 27, also referred to herein as 1211), PLTGRSGG (SEQ ID NO: 28, also referred to herein as 1214), LTGRSGA (SEQ ID NO: 29, also referred to herein as Consensus 2), AARGPAIH (SEQ ID NO: 30, also referred to herein as 1217), RGPAFNPM (SEQ ID NO: 31, also referred to herein as 1219), SSRGPAYL (SEQ ID NO: 32, also referred to herein as 1196), RGPATPIM (SEQ ID NO: 33, also referred to herein as 1201), RGPA (SEQ ID NO: 34, also referred to herein as Consensus 3); GGQPSGMWGW (SEQ ID NO: 38); FPRPLGITGL (SEQ ID NO: 39); VHMPLGFLGP (SEQ ID NO: 40); SPLTGRSG (SEQ ID NO: 41); SAGFSLPA (SEQ ID NO: 42); LAPLGLQRR (SEQ ID NO: 43); SGGPLGVR (SEQ ID NO: 44); and/or PLGL (SEQ ID NO: 45).

In embodiments where the CL includes an amino acid sequence that is a substrate for legumain, the substrate can include an amino acid sequence or can be derived from an amino acid sequence such as, for example AANL (SEQ ID NO: 35) and PTNL (SEQ ID NO: 36).

In some embodiments, the CL is selected for use with a specific protease, for example a protease that is known to be co-localized with the target of the activatable antibody. For example, suitable CLs for use in the activatable antibodies of the disclosure are cleaved by at least a protease such as urokinase, legumain, and/or MT-SP1 (matriptase) and include the sequence.

Flexible portions suitable for use in compositions described herein are generally ones that provide flexibility of the activatable antibody to facilitate the inhibition of the binding of the AB to the target. Such flexible portions are also referred to herein as flexible peptide portions. Suitable flexible portions are readily selected and are of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible portions include glycine polymers $(G)_n$, glycine-serine polymers (including, for example, $(GS)_n$, $(GSGGS)_n$ (SEQ ID NO: 5) and $(GGGS)_n$ (SEQ ID NO: 6), where n is an integer of at least one), glycine-alanine polymers, alanine-serine polymers, and other flexible peptide sequences known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible portions include, but are not limited to Gly-Gly-Ser-Gly (SEQ ID NO: 7), Gly-Gly-Ser-Gly-Gly (SEQ ID NO: 8), Gly-Ser-Gly-Ser-Gly (SEQ ID NO: 9), Gly-Ser-Gly-Gly-Gly (SEQ ID NO: 10), Gly-Gly-Gly-Ser-Gly (SEQ ID NO: 11), Gly-Ser-Ser-Ser-Gly (SEQ ID NO: 12), (Glu-Gly-Gly-Gly-Ser (SEQ ID NO: 13) and the like. The ordinarily skilled artisan will recognize that design of an activatable antibody can include cleavable linkers (CLs) that are all or partially flexible, such that the CL can include a flexible portion as well as one or more portions that confer less flexible structure to provide for a desired activatable antibody structure.

In addition to the elements described above, the activatable antibody can contain additional elements such as, for example, amino acid sequence N- or C-terminal of the AA. For example, the activatable antibody can include a detectable label or other moiety, a targeting moiety to facilitate delivery to a cell or tissue of interest or the activatable antibody can be provided in the context of a scaffold protein to facilitate display of the AA on a cell surface.

In some embodiments, activatable antibodies may be made biosynthetically using recombinant DNA technology and expression in eukaryotic or prokaryotic species. The cDNAs encoding the non-binding steric moieties (NB) or binding partners (BP) for non-binding steric moieties, the linker sequence (which may include a cleavable linker (CL), and antibody chain (heavy or light)) can be linked in an 5' to 3' (N- to C-terminal in the translated product) sequence to create the nucleic acid construct, which is expressed as the activatable antibody protein following a conventional antibody expression process. In some embodiments, the activatable antibody could be semi-synthetically produced by expressing a CL-antibody and then coupling the NB or BP chemically at or near the N-terminus of the protein. In some embodiments, the activatable antibody could be produced by expressing an antibody and then coupling the NB or BP and the CL chemically at or near the N-terminus of the protein such that the activatable antibody in the uncleaved state has the structural arrangement from N-terminus to C-terminus as follows: NB-CL-AB, AB-CL-NB, BP-CL-AB or AB-CL-BP.

The invention also provides nucleic acid constructs that include sequences coding for activatable antibodies. Suitable nucleic acid constructs include, but are not limited to, constructs that are capable of expression in a prokaryotic or eukaryotic cell. Expression constructs are generally selected so as to be compatible with the host cell in which they are to be used. For example, non-viral and/or viral constructs vectors may be prepared and used, including plasmids, which provide for replication of an AA- or candidate AA-encoding DNA and/or expression in a host cell. The choice of vector will depend on the type of cell in which propagation is desired and the purpose of propagation. Certain constructs are useful for amplifying and making large amounts of the desired DNA sequence. Other vectors are suitable for expression in cells in culture. The choice of appropriate vector is well within the skill of the art. Many such vectors are available commercially. Methods for generating constructs can be accomplished using methods well known in the art.

To enable expression in a host cell, the polynucleotide encoding an activatable antibody is operably linked to a regulatory sequence as appropriate to facilitate the desired expression properties. These regulatory sequences can include promoters, enhancers, terminators, operators, repressors, silencers, inducers, and 3' or 5' UTRs. Expression constructs generally also provide a transcriptional and translational initiation region as may be needed or desired, which may be inducible or constitutive, where the coding region is operably linked under the transcriptional control of the transcriptional initiation region, and a transcriptional and translational termination region. These control regions may be native to the species from which the nucleic acid is obtained, or may be derived from exogenous sources.

Promoters may be either constitutive or regulatable. In some situations it may be desirable to use conditionally active promoters, such as inducible promoters, e.g., temperature-sensitive promoters. Inducible elements are DNA sequence elements that act in conjunction with promoters and may bind either repressors (e.g. lacO/LAC Iq repressor system in $E.$ $coli$) or inducers (e.g., gal1/GAL4 inducer system in yeast). In such cases, transcription is virtually shut off until the promoter is de-repressed or induced, at which point transcription is turned-on.

Constructs, including expression constructs, can also include a selectable marker operative in the host to facilitate, for example, growth of host cells containing the construct of interest. Such selectable marker genes can provide a phenotypic trait for selection of transformed host cells such as dihydrofolate reductase or neomycin resistance for eukaryotic cell culture.

Expression constructs can include convenient restriction sites to provide for the insertion and removal of nucleic acid sequences encoding the activatable antibody. Alternatively or in addition, the expression constructs can include flanking sequences that can serve as the basis for primers to facilitate nucleic acid amplification (e.g., PCR-based amplification) of an activatable antibody-coding sequence of interest.

The above described expression systems may be employed with prokaryotes or eukaryotes in accordance with conventional ways, depending upon the purpose for expression. In some embodiments, a unicellular organism, such as $E.$ $coli,$ $B.$ $subtilis,$ $S.$ $cerevisiae,$ insect cells in combination with baculovirus vectors, or cells of a higher organism such as vertebrates, e.g. COS 7 cells, HEK 293, CHO, $Xenopus$ $Oocytes,$ etc., may be used as the expression host cells. Expression systems for each of these classes and types of host cells are known in the art.

The activatable antibodies, in some embodiments, are conjugated to an agent, for example, a therapeutic agent or a diagnostic agent, to produce an activatable antibody conjugate. The agent is attached either directly or via a linker to the AB. Such agents or linkers are selectively attached to those areas of ABs which are not a part of nor directly involved with the antigen binding site of the molecule.

The additional agent, e.g., therapeutic agent or diagnostic agent, used in the activatable antibody conjugate is chosen based on a desired characteristic or biological outcome. For example, when delivery and release of the agent conjugated to the AB are desired, immunoglobulin classes that are known to activate complement are used. In other applications, carrier immunoglobulins that do not result in complement activation are used. For example, suitable immunoglobulin carriers include certain classes of antibodies such IgM, IgA, IgD, IgE; certain subclasses of IgG; or certain fragments of immunoglobulins, e.g., half ABs (a single heavy: light chain pair), or Fab or F(ab')$_2$ fragments.

The additional agent, e.g., therapeutic agent and/or diagnostic agent, is linked to the activatable antibody using any known method by which the resulting activatable antibody conjugate retains the ability to bind antigen and to activate the complement cascade (when the unconjugated AA also had such ability). As a result, when the activatable antibody conjugate is administered to an individual, the subsequent formation of immune complexes with target antigens in vivo can activate the individual's serum complement system. The linker is designed to be susceptible to cleavage by complement and so the agent can be cleaved at the target site by one or more of the enzymes of the complement cascade. The majority of the release of the agent occurs following delivery to the target site.

The additional agent, e.g., therapeutic agent and/or diagnostic agent, is any agent that retains its essential properties after reaction with the AB and enables the AB to substantially retain immunospecificity and immunoreactivity. The additional agent, e.g., therapeutic agent and/or diagnostic agent, does not significantly affect the activatable function of the activatable antibodies described herein.

The additional agent, e.g., therapeutic agent and/or diagnostic agent, for use in the activatable antibody conjugate is selected according to the purpose of the intended application (e.g., killing, prevention of cell proliferation, hormone therapy or gene therapy, or diagnosis). Such agents may include but are not limited to, for example, pharmaceutical agents, toxins, fragments of toxins, alkylating agents, enzymes, antibiotics, antimetabolites, antiproliferative agents, hormones, neurotransmitters, DNA, RNA, siRNA, oligonucleotides, antisense RNA, aptamers, diagnostics, radioopaque dyes, radioactive isotopes, fluorogenic compounds, magnetic labels, nanoparticles, marker compounds, lectins, compounds which alter cell membrane permeability, photochemical compounds, small molecules, liposomes, micelles, gene therapy vectors, viral vectors, and the like. Non-limiting examples of suitable additional agents are shown below in Table 4. Finally, combinations of agents or combinations of different classes of agents may be used in the activatable antibody conjugates.

Table 4 lists some of the exemplary pharmaceutical agents that may be employed in the herein described invention but in no way is meant to be an exhaustive list.

TABLE 4

Exemplary Pharmaceutical Agents for Conjugation

| CYTOTOXIC AGENTS | |
| --- | --- |
| Auristatins | Turbo statin |
| Auristatin E | Phenstatins |
| Monomethyl auristatin E (MMAE) | Hydroxyphenstatin |
| Desmethyl auristatin E (DMAE) | Spongistatin 5 |
| Auristatin F | Spongistatin 7 |
| Monomethyl auristatin F (MMAF) | Halistatin 1 |
| Desmethyl auristatin F (DMAF) | Halistatin 2 |
| Auristatin derivatives, e.g., amides thereof | Halistatin 3 |
| Auristatin tyramine | Modified Bryostatins |
| Auristatin quinoline | Halocomstatins |
| Dolastatins | Pyrrolobenzimidazoles (PBI) |
| Dolastatin derivatives | Cibrostatin6 |
| Dolastatin 16 DmJ | Doxaliform |
| Dolastatin 16 Dpv | Anthracyclins analogues |
| Maytansinoids, e.g. DM-1; DM-4 | Anthracyclins analogues |
| Maytansinoid derivatives | |
| Duocarmycin | Cemadotin analogue (CemCH2-SH) |
| Duocarmycin derivatives | Pseudomonas toxin A (PE38) variant |
| Alpha-amanitin | Pseudomonas toxin A (ZZ-PE38) variant |
| Anthracyclines | ZJ-101 |
| Doxorubicin | OSW-1 |
| Daunorubicin | 4-Nitrobenzyloxycarbonyl Derivatives of O6-Benzylguanine |
| Bryostatins | Topoisomerase inhibitors |
| Camptothecin | Hemiasterlin |
| Camptothecin derivatives | Cephalotaxine |
| 7-substituted Camptothecin | Homoharringtonine |
| 10, 11-Difluoromethylene-dioxycamptothecin | Pyrrolobenzodiazepine dimers (PBDs) |
| Combretastatins | Functionalized pyrrolobenzodiazepenes |
| Debromoaplysiatoxin | Calicheamicins |

TABLE 4-continued

Exemplary Pharmaceutical Agents for Conjugation

| Kahalalide-F | Podophyllotoxins |
| --- | --- |
| Discodermolide | Taxanes |
| Ecteinascidins | Vinca alkaloids |
| ANTIVIRALS | CONJUGATABLE DETECTION REAGENTS |
| Acyclovir | Fluorescein and derivatives thereof |
| Vira A | Fluorescein isothiocyanate (FITC) |
| Symmetrel | |
| ANTIFUNGALS | |
| Nystatin | |
| ADDITIONAL ANTI-NEOPLASTICS | RADIOPHARMACEUTICALS |
| Adriamycin | $^{125}$I |
| Cerubidine | $^{131}$I |
| Bleomycin | $^{89}$Zr |
| Alkeran | $^{111}$In |
| Velban | $^{123}$I |
| Oncovin | $^{131}$I |
| Fluorouracil | $^{99m}$Tc |
| Methotrexate | $^{201}$Tl |
| Thiotepa | $^{133}$Xe |
| Bisantrene | $^{11}$C |
| Novantrone | $^{62}$Cu |
| Thioguanine | $^{18}$F |
| Procarabizine | $^{68}$Ga |
| Cytarabine | $^{13}$N |
| | $^{15}$O |
| ANTI-BACTERIALS | $^{38}$K |
| Aminoglycosides | $^{82}$Rb |
| Streptomycin | $^{99m}$Tc (Technetium) |
| Neomycin | |
| Kanamycin | HEAVY METALS |
| Amikacin | Barium |
| Gentamicin | Gold |
| Tobramycin | Platinum |
| Streptomycin B | |
| Spectinomycin | ANTI-MYCOPLASMALS |
| Ampicillin | Tylosine |
| Sulfanilamide | Spectinomycin |
| Polymyxin | |
| Chloramphenicol | |

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments, the binding is covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly suitable linkers include: (i) SMPT (4-succinimidyloxycarbonyl-alpha-methyl-alpha-(2-pridyl-dithio)-toluene (Pierce Chem. Co., Cat. (21558G); (ii) SPDP (succinimidyl-6 [3-(2-pyridyldithio) propionamido]hexanoate (Pierce Chem. Co., Cat #21651G); and (iii) Sulfo-LC-SPDP (sulfosuccinimidyl 6 [3-(2-pyridyldithio)-propianamide] hexanoate (Pierce Chem. Co. Cat. #2165-G.

The linkers described above contain components that have different attributes, thus leading to conjugates with differing physio-chemical properties. For example, the linker SMPT contains a sterically hindered disulfide bond, and can form conjugates with increased stability. Disulfide linkages, are in general, less stable than other linkages because the disulfide linkage is cleaved in vitro, resulting in less conjugate available.

The reagent EDC (1-ethyl-3-(3-dimethylaminopropyl) carbodiimide hydrochloride is useful to create a carboxamide starting with a carboxylic acid and a primary or secondary amine. Thus, EDC may be used to link lysine residues in an antibody with a carboxylic acid in a linker or toxin, or to link aspartate or glutamate residues in an antibody with an amine in a linker or toxin. Such conjugation reactions utilizing EDC may be enhanced by addition of NHS (N-hydroxysuccinimide) or sulfo-NHS (N-hydroxy-3-oxysulfonylsuccinimide). Addition of NHS or sulfo-NHS to such conjugation reactions may enhance the rate, completeness, selectivity, and/or reproducibility of the conjugation reactions.

In some embodiments, the linkers are cleavable. In some embodiments, the linkers are non-cleavable. In some embodiments, two or more linkers are present. The two or more linkers are all the same, e.g., cleavable or non-cleavable, or the two or more linkers are different, e.g., at least one cleavable and at least one non-cleavable.

The present invention utilizes several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. According to the invention, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present invention, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

According to the present invention, suitable linkers for attachment to neither oxidized nor reduced Abs include those having certain functional groups capable of reaction with the primary amino groups present in unmodified lysine residues in the Ab. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present invention, suitable linkers for attachment to neither oxidized nor reduced Abs include those having certain functional groups capable of reaction with the carboxylic acid groups present in aspartate or glutamate residues in the Ab, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In other embodiments the AB is first attached to the MM, CM and associated linkers and then attached to the linker for conjugation purposes.

Branched Linkers: In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

Alternatively, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers: Peptide linkers that are susceptible to cleavage by enzymes of the complement system, such as but not limited to urokinase, tissue plasminogen activator, trypsin, plasmin, or another enzyme having proteolytic activity may be used in one embodiment of the present invention. According to one method of the present invention, an agent is attached via a linker susceptible to cleavage by complement. The antibody is selected from a class that can activate complement. The antibody-agent conjugate, thus, activates the complement cascade and releases the agent at the target site. According to another method of the present invention, an agent is attached via a linker susceptible to cleavage by enzymes having a proteolytic activity such as a urokinase, a tissue plasminogen activator, plasmin, or trypsin. These cleavable linkers are useful in conjugated activatable antibodies that include an extracellular toxin, e.g., by way of non-limiting example, any of the extracellular toxins shown in Table 4.

Non-liming examples of cleavable linker sequences are provided in Table 5.

TABLE 5

Exemplary Linker Sequences for Conjugation

| Types of Cleavable Sequences | Amino Acid Sequence |
|---|---|
| Plasmin cleavable sequences | |
| Pro-urokinase | PRFKIIGG (SEQ ID NO: 46) |
|  | PRFRIIGG (SEQ ID NO: 47) |
| TGFβ | SSRHRRALD (SEQ ID NO: 48) |
| Plasminogen | RKSSIIIRMRDVVL (SEQ ID NO: 49) |
| Staphylokinase | SSSFDKGKYKKGDDA (SEQ ID NO: 50) |
|  | SSSFDKGKYKRGDDA (SEQ ID NO: 51) |
| Factor Xa cleavable sequences | |
|  | IEGR (SEQ ID NO: 52) |
|  | IDGR (SEQ ID NO: 53) |
|  | GGSIDGR (SEQ ID NO: 54) |
| MMP cleavable sequences | |
| Gelatinase A | PLGLWA (SEQ ID NO: 55) |
| Collagenase cleavable sequences | |
| Calf skin collagen (α1(I) chain) | GPQGIAGQ (SEQ ID NO: 56) |
| Calf skin collagen (α2(I) chain) | GPQGLLGA (SEQ ID NO: 57) |
| Bovine cartilage collagen (α1(II) chain) | GIAGQ (SEQ ID NO: 58) |
| Human liver collagen (α1(III) chain) | GPLGIAGI (SEQ ID NO: 59) |
| Human α₂M | GPEGLRVG (SEQ ID NO: 60) |
| Human PZP | YGAGLGVV (SEQ ID NO: 61) |
|  | AGLGVVER (SEQ ID NO: 62) |
|  | AGLGISST (SEQ ID NO: 63) |
| Rat α₁M | EPQALAMS (SEQ ID NO: 64) |
|  | QALAMSAI (SEQ ID NO: 65) |
| Rat α₂M | AAYHLVSQ (SEQ ID NO: 66) |
|  | MDAFLESS (SEQ ID NO: 67) |
| Rat α₁I₃(2J) | ESLPVVAV (SEQ ID NO: 68) |

TABLE 5-continued

Exemplary Linker Sequences for Conjugation

| Types of Cleavable Sequences | Amino Acid Sequence |
|---|---|
| Rat α₁I₃(27J) | SAPAVESE (SEQ ID NO: 69) |
| Human fibroblast collagenase (autolytic cleavages) | DVAQFVLT (SEQ ID NO: 70) |
|  | VAQFVLTE (SEQ ID NO: 71) |
|  | AQFVLTEG (SEQ ID NO: 72) |
|  | PVQPIGPQ (SEQ ID NO: 73) |

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In certain specific embodiments the reducing agent that would modify a CM would also modify the linker of the conjugated activatable antibody.

Spacers and Cleavable Elements:

In still another embodiment, it may be necessary to construct the linker in such a way as to optimize the spacing between the agent and the AB of the activatable antibody. This may be accomplished by use of a linker of the general structure:

$$W\text{—}(CH_2)n\text{-}Q$$

wherein
W is either —NH—CH₂— or —CH₂—;
Q is an amino acid, peptide; and
n is an integer from 0 to 20.

In still other embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

Serum Complement and Selection of Linkers:

According to one method of the present invention, when release of an agent is desired, an AB that is an antibody of a class that can activate complement is used. The resulting conjugate retains both the ability to bind antigen and activate the complement cascade. Thus, according to this embodiment of the present invention, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 4.

Linkers for Release without Complement Activation:

In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers:

In other embodiments, the activatable antibody may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bis-sialyl ether. Other suitable linkers include cathepsin-labile substrates, particularly those that show optimal function at an acidic pH.

Exemplary hetero-bifunctional cross-linkers are referenced in Table 6.

TABLE 6

Exemplary Hetero-Bifunctional Cross Linkers

HETERO-BIFUNCTIONAL CROSS-LINKERS

| Linker | Reactive Toward | Advantages and Applications | Spacer Arm Length after cross-linking (Angstroms) |
|---|---|---|---|
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extender spacer arm Water-soluble | 15.6 Å |
| SMCC | Primary amines | Stable maleimide reactive group | 11.6 Å |

TABLE 6-continued

Exemplary Hetero-Bifunctional Cross Linkers

HETERO-BIFUNCTIONAL CROSS-LINKERS

| Linker | Reactive Toward | Advantages and Applications | Spacer Arm Length after cross-linking (Angstroms) |
|---|---|---|---|
| | Sulfhydryls | Enzyme-antibody conjugation Hapten-carrier protein conjugation | |
| Sulfo-SMCC | Primary amines Sulfhydryls | Stable maleimide reactive group Water-soluble Enzyme-antibody conjugation | 11.6 Å |
| MBS | Primary amines Sulfhydryls | Enzyme-antibody conjugation Hapten-carrier protein conjugation | 9.9 Å |
| Sulfo-MBS | Primary amines Sulfhydryls | Water-soluble | 9.9 Å |
| SIAB | Primary amines Sulfhydryls | Enzyme-antibody conjugation | 10.6 Å |
| Sulfo-SIAB | Primary amines Sulfhydryls | Water-soluble | 10.6 Å |
| SMPB | Primary amines Sulfhydryls | Extended spacer arm Enzyme-antibody conjugation | 14.5 Å |
| Sulfo-SMPB | Primary amines Sulfhydryls | Extended spacer arm Water-soluble | 14.5 Å |
| EDE/Sulfo-NHS | Primary amines Carboxyl groups | Hapten-Carrier conjugation | 0 |
| ABH | Carbohydrates Nonselective | Reacts with sugar groups | 11.9 Å |

Non-Cleavable Linkers or Direct Attachment:

In still other embodiments of the invention, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds that may be modified to include functional groups that can subsequently be utilized in attachment to ABs by the methods described herein. A general formula for such an organic linker could be

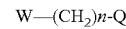

W—(CH$_2$)$n$-Q wherein
W is either —NH—CH$_2$— or —CH$_2$—;
Q is an amino acid, peptide; and
n is an integer from 0 to 20.

Non-Cleavable Conjugates:

Alternatively, a compound may be attached to ABs that do not activate complement. When using ABs that are incapable of complement activation, this attachment may be accomplished using linkers that are susceptible to cleavage by activated complement or using linkers that are not susceptible to cleavage by activated complement.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

The activatable antibody conjugates of the invention are useful in therapeutics, diagnostics, substrate modification and the like.

For example, the activatable antibody conjugates are useful in a variety of therapeutic and/or diagnostic in vivo applications such as, by way of non-limiting example, treatment and/or diagnosis of neoplasms, including cancers, adenomas, and hyperplasias; certain immunological disorders, including autoimmune diseases, graft-versus-host diseases (e.g., after bone marrow transplantation), immune suppressive diseases, e.g., after kidney or bone marrow transplantation. Treatment of such cellular disorders involving, for example, bone marrow transplantation, may include purging (by killing) undesired cells, e.g., malignant cells or mature T lymphocytes. In some embodiments, the activatable antibody conjugates are used in the treatment and/or diagnosis of an inflammatory disease such as rheumatoid arthritis (RA) or fibrosis.

Therapeutic applications center generally on treatment of various cellular disorders, including those broadly described above, by administering an effective amount of the antibody-agent conjugates of the invention. The properties of the antibody are such that it is immunospecific for and immunoreactive with a particular antigen render it ideally suited for delivery of agents to specific cells, tissues, organs or any other site having that particular antigen. Thus, the activatable antibody conjugate functions to deliver the conjugate to the target site.

The choice of ABs, linkers, and agents used to make the activatable antibody conjugates depends upon the purpose of delivery. The delivery and release or activation of agents at specific target sites may result in selective killing or inhibition of proliferation of tumor cells, cancer cells, fungi, bacteria, parasites, or virus. The targeted delivery of hormones, enzymes, or neurotransmitters to selected sites may also be accomplished. Additionally, the conjugates may be used to reduce or prevent the activation of oncogenes, such as myc, ras and the like.

Administration of activatable antibody conjugates uses any suitable adjuvant including, but not limited to, serum or physiological saline, with or without another protein, such as human serum albumin. Dosage of the conjugates may readily be determined by one of ordinary skill, and may differ depending upon the nature of the cellular disorder and the agent used. Route of administration may be parenteral, with intravenous administration generally suitable.

The activatable antibodies and activatable antibody conjugates can be incorporated into pharmaceutical compositions containing, for example, a therapeutically effective amount of an activatable antibody or activatable antibody conjugate of interest and a carrier that is a pharmaceutically acceptable excipient (also referred to as a pharmaceutically acceptable carrier). Many pharmaceutically acceptable excipients are known in the art, and are generally selected according to the route of administration, the condition to be treated, the site where treatment and/or diagnosis can be effected, and other such variables that are well understood in the art. Pharmaceutically acceptable excipients have been amply described in a variety of publications, including, for example, A. Gennaro (2000) Remington: The Science and Practice of Pharmacy, 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc. Pharmaceutical compositions can also include other components such as pH adjusting and buffering agents, tonicity adjusting agents, stabilizers, wetting agents and the like. In some embodiments, nanoparticles or liposomes carry a pharmaceutical composition that includes an activatable antibody or activatable antibody conjugate.

In general, pharmaceutical formulations of one or more activatable antibodies or activatable antibody conjugates are prepared for storage by mixing the activatable antibody or activatable antibody conjugate having a desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations to be used for in vivo administration must be sterile. This is readily accomplished by filtration through sterile filtration membranes. Pharmaceutical formulations may also contain more than one active compound as necessary for the particular indication being treated and/or diagnosed, where the additional active compounds generally are those with activities complementary to an activatable antibody or activatable antibody conjugate. Such compounds are suitably present in combination in amounts that are effective for the purpose intended.

The pharmaceutical formulation are to be provided in a variety of dosage forms such as a systemically or local injectable preparation. The components can be provided in a carrier such as a microcapsule, e.g., such as that prepared by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980).

Sustained-release preparations are also within the scope of an activatable antibody-containing formulations or activatable antibody conjugate-containing formulations. Exemplary sustained-release preparations can include semi-permeable matrices of solid hydrophobic polymers containing the activatable antibody or activatable antibody conjugate, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

When encapsulated activatable antibodies or activatable antibody conjugates remain in the body for a long time, they may denature or aggregate as a result of exposure to moisture at physiological temperature (~37° C.), resulting in decreased biological activity and possible changes in immunogenicity. Rational strategies can be devised for stabilization depending on the mechanism involved. For example, if the aggregation mechanism is discovered to be undesirable intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Activatable antibodies or activatable antibody conjugates can be conjugated to delivery vehicles for targeted delivery of an active agent that serves a therapeutic purpose. Activatable antibodies or activatable antibody conjugates can be conjugated to delivery vehicles for targeted delivery of an active agent that serves a diagnosis purpose or other detection purpose. For example, activatable antibodies or activatable antibody conjugates can be conjugated to nanoparticles or liposomes having drugs encapsulated therein or associated therewith. In this manner, specific, targeted delivery of the drug can be achieved. Methods of linking polypeptides to liposomes are well known in the art and such methods can be applied to link activatable antibody or activatable antibody conjugates to liposomes for targeted and or selective delivery of liposome contents. By way of example, polypeptides can be covalently linked to liposomes through thioether bonds. PEGylated gelatin nanoparticles and PEGylated liposomes have also been used as a support for the attachment of polypeptides, e.g., single chain antibodies. See e.g., Immordino et al. (2006) Int J Nanomedicine. September; 1(3): 297-315, incorporated by reference herein for its disclosure of methods of conjugating polypeptides, e.g., antibody fragments, to liposomes.

Activatable antibodies and activatable antibody conjugates described herein are selected for use in methods of treatment and/or diagnosis of suitable subjects according to the CL-AB combination provided in the activatable antibody or activatable antibody conjugate. The activatable antibody or activatable antibody conjugate is administered by any suitable means, including oral, parenteral, subcutaneous, intraperitoneal, intrapulmonary, and intranasal, and, if desired for local injection (e.g., at the site of a solid tumor). Parenteral administration routes include intramuscular, intravenous, intraarterial, intraperitoneal, or subcutaneous administration.

The terms treatment site and diagnostic site are meant to refer to sites at which an activatable antibody or activatable antibody conjugate is designed to be switchable, as described herein, e.g., a site at which a target for the AB of an activatable antibody or activatable antibody conjugate and an agent that cleaves the CL are co-localized. Treatment sites and/or diagnostic sites include tissues that are accessed by local administration (e.g., injection, infusion (e.g., by catheter), etc.) or by systemic administration (e.g., administration to a site remote from a treatment site and/or a diagnostic site). Treatment sites and/or diagnostic sites include those that are relatively biologically confined (e.g., an organ, sac, tumor site, and the like).

The appropriate dosage of an activatable antibody or activatable antibody conjugate will depend on the type of disease to be treated, the severity and course of the disease, the patient's clinical history and response to the activatable antibody or activatable antibody conjugate, and the discretion of the attending physician. Activatable antibodies or activatable antibody conjugates can suitably be administered to the patient at one time or over a series of treatments. Activatable antibodies or activatable antibody conjugates can be administered along with other treatments and modes of therapies, other diagnostics and modes of diagnosis, other pharmaceutical agents, and the like.

Depending on the type and severity of the disease, about 1 µg/kg to 15 mg/kg (e.g., 0.1-20 mg/kg) of an activatable antibody or activatable antibody conjugate can serve as an initial candidate dosage for administration to the patient, whether, for example, by one or more separate administrations, or by continuous infusion. A typical daily dosage might range from about 1 µg/kg to 100 mg/kg or more, depending on factors such as those mentioned herein. For repeated administrations over several days or longer, depending on the condition, the treatment is sustained until a desired suppression of disease symptoms occurs. However, other dosage regimens may be useful.

The activatable antibody or activatable antibody conjugate composition will be formulated, dosed, and administered in a fashion consistent with good medical practice. Factors for consideration in this context include the particular disorder being treated and/or diagnosed, the particular mammal being treated and/or diagnosed, the clinical condition of the individual patient, the cause of the disorder, the site of delivery of the activatable antibody or activatable antibody conjugate, the method of administration, the scheduling of administration, and other factors known to medical practitioners. The therapeutically effective amount of an activatable antibody or activatable antibody conjugate to be administered will be governed by such considerations, and is the minimum amount necessary to prevent, ameliorate, or treat a disease or disorder. The diagnostically effective amount of an activatable antibody or activatable antibody conjugate to be administered will be governed by such considerations, and is the minimum amount necessary to diagnose a disease or disorder.

Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this invention can be used to prevent the onset or reoccurrence of the disease or disorder in a subject, e.g., a human or other mammal, such as a non-human primate, companion animal (e.g., cat, dog, horse), farm animal, work animal, or zoo animal.

Activatable antibodies or activatable antibody conjugates can be used in combination (e.g., in the same formulation or in separate formulations) with one or more additional therapeutic agents, one or more treatment methods, one or more diagnostic agents, or one or more diagnostic methods (i.e., combination therapy). An activatable antibody or activatable antibody conjugate can be administered in admixture with another therapeutic agent or diagnostic agent or can be administered in a separate formulation. Therapeutic agents and/or treatment methods that can be administered or otherwise used in combination with an activatable antibody or activatable antibody conjugate, and which are selected according to the condition to be treated, include surgery (e.g., surgical removal of cancerous tissue), radiation therapy, bone marrow transplantation, chemotherapeutic treatment, certain combinations of the foregoing, and the like. Diagnostic agents and/or diagnostic methods that can be administered or otherwise used in combination with an activatable antibody or activatable antibody conjugate, and which are selected according to the condition to be diagnosed, include physical examination, laboratory and other clinical assays or other tests, certain combinations of the foregoing, and the like. Combinations can be co-administered or administered sequentially as appropriate.

Unless otherwise defined, scientific and technical terms used in connection with the present invention shall have the meanings that are commonly understood by those of ordinary skill in the art. The term "a" entity or "an" entity refers to one or more of that entity. For example, a compound refers to one or more compounds. As such, the terms "a", "an", "one or more" and "at least one" can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment and/or diagnosis of patients. The term patient includes human and veterinary subjects.

The invention will be further described in the following examples, which do not limit the scope of the invention described in the claims.

EXAMPLES

Example 1. Construction of a Binding Partner (BP)-Activatable Antibody

A BP-activatable antibody referred to herein as activatable antibody "ABP-1203-C225," which includes the albumin-binding peptide (ABP) SA06 (Dennis et al., J. Biol. Chem. 277, 35035(2002)) linked to the anti-EGFR antibody C225 (Li et al., Cancer Cell 7, 301 (2005)), was made using recombinant DNA technology. Specifically, the following components were used: a nucleic acid molecule encoding the albumin-binding peptide SA06 (QRLMEDICLPRWGCLWEDDF) (SEQ ID NO: 1) fused to a flexible portion (FP1) having the sequence GSSGGSGGSGGSGGGSGGGSGG (SEQ ID NO: 2), a cleavable linker (CL) referred to herein as 1203 having the sequence TGRGPSWV (SEQ ID NO: 3), which is cleaved by human urokinase plasminogen activator (uPA), a second flexible portion (FP2) having the sequence GG, and the N-terminus of the C225 antibody light chain. The BP-activatable antibody was constructed using techniques similar to those described in PCT International Publication Numbers WO 2009/025846 A2, published 26 Feb. 2009, and WO 2010/081173 A2, published 15 Jul. 2010, each of which is incorporated herein in its entirety. Briefly, the nucleic acid molecule encoding ABP-1203-C225 was inserted into a modified pcDNA3.1 mammalian expression vector (Invitrogen Corp., Carlsbad, Calif.), and ABP-1203-C225 was expressed in CHO-S cells (Invitrogen). The amino acid sequence of the resultant activatable antibody is:

```
(c225-LC)
                                            (SEQ ID NO: 4)
QRLMEDICLPRWGCLWEDDFGSSGGSGGSGGSGTGRGPSWVG
GTQ . . . .
```

Two sequences of the ABP-1203-C225 activatable antibody are shown below, Sequence 1 is the sequence of a version of the ABP-1203-C225 activatable antibody that does not include a signal peptide, and Sequence 2 is the sequence of the ABP-1203-C225 activatable antibody that includes a signal peptide:

```
ABP-1203-C225 Heavy Chain DNA Sequence 1
[C225]
                                            (SEQ ID NO: 14)
[caggtgcagctgaaacagagcggcccgggcctggtgcagccgagccagagcctgagcattacc tgcaccgtgagcggctttagcctgaccaactatggcgtgcattgggtgcgccagagcccgggca aaggcctggaatggctgggcgtgatttggagcggcggcaacaccgattataacaccccgtttac cagccgcctgagcattaacaaagataacagcaaaagccaggtgttttttaaaatgaacagcctg caaagcaacgataccgcgatttattattgcgcgcgcgcgctgacctattatgattatgaatttg cgtattggggccagggcaccctggtgaccgtgagcgcggctagcaccaagggcccatcggtctt
```

-continued

```
cccctggcaccctcctccaagagcacctctgggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg aactcctggggggaccgtcagtcttcctcttccccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtaca acagcacgtaccgtgtggtcagcgtcctcaccgtcctgcaccaggactggctgaatggcaagga gtacaagtgcaaggtctccaacaaagcccccagccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]
```

ABP-1203-C225 Heavy Chain Amino Acid Sequence 1
[C225]
(SEQ ID NO: 15)

[QVQLKQSGPG LVQPSQSLSI TCTVSGFSLT NYGVHWVRQS PGKGLEWLGV

IWSGGNTDYN TPFTSRLSIN KDNSKSQVFF KMNSLQSNDT AIYYCARALT

YYDYEFAYWG QGTLVTVSAA STKGPSVFPL APSSKSTSGG TAALGCLVKD

YFPEPVTVSW NSGALTSGVH TFPAVLQSSG LYSLSSVVTV PSSSLGTQTY

ICNVNHKPSN TKVDKKVEPK SCDKTHTCPP CPAPELLGGP SVFLFPPKPK

DTLMISRTPE VTCVVVDVSH EDPEVKFNWY VDGVEVHNAK TKPREEQYNS

TYRVVSVLTV LHQDWLNGKE YKCKVSNKAL PAPIEKTISK AKGQPREPQV

YTLPPSRDEL TKNQVSLTCL VKGFYPSDIA VEWESNGQPE NNYKTTPPVL

DSDGSFFLYS KLTVDKSRWQ QGNVFSCSVM HEALHNHYTQ KSLSLSPGK*]

ABP-1203-C225 Light Chain DNA Sequence 1
[ABP (SEQ ID NO: 74)][FP1 (SEQ ID NO: 75)][Substrate 1203 (SEQ
ID NO: 76)][FP2 (SEQ ID NO: 77)][C225 (SEQ ID NO: 14)]
(SEQ ID NO: 16)
[cagagactgatggaggacatctgcctgccgagatggggatgcctgtgggaagacgacttc]

[ggctcgagcggtggcagcggtggctctggtggatccggt][*actggccgtggtccaagctggg*

*tt*][ggcggtacc][cagatcttgctgacccagagcccggtgattctgagcgtgagcccgggcg aacgtgtgagctttagctgccgcgcgagccagagcattggcaccaacattcattggtatcagca gcgcaccaacggcagcccgcgcctgctgattaaatatgcgagcgaaagcattagcggcattccg agccgctttagcggcagcggcagcggcaccgattttaccctgagcattaacagcgtggaaagcg aagatattgcggattattattgccagcagaacaacaactggccgaccacctttggcgcgggcac caaactggaactgaaacgtacggtggctgcaccatctgtcttcatcttcccgccatctgatgag cagttgaaatctggaactgcctctgttgtgtgcctgctgaataacttctatcccagagaggcca aagtacagtggaaggtggataacgccctccaatcgggtaactcccaggagagtgtcacagagca ggacagcaaggacagcacctacagcctcagcagcaccctgacgctgagcaaagcagactacgag
``` aaacacaaagtctacgcctgcgaagtcacccatcagggcctgagctcgcccgtcacaaagagct tcaacaggggagcgtag]
Bold:              Albumin binding peptide
Underline:         Flexible Portion 1 (FP1)
Italics:           1203 Substrate
Double Underline:  Flexible Portion 2 (FP2)
Normal text:       C225

ABP-1203-C225 Light Chain Amino Acid Sequence 1
[ABP (SEQ ID NO: 1)][FP1 (SEQ ID NO: 78)][Substrate 1203 (SEQ ID
NO: 3)][FP2 (SEQ ID NO: 79)][C225 (SEQ ID NO: 15)]

(SEQ ID NO: 17)

[QRLMEDICLP RWGCLWEDDF][GSSGGSGGSG GSG][*TGRGPSW V*][GGT]

[QILLTQ SPVILSVSPG ERVSFSCRAS QSIGTNIHWY QQRTNGSPRL

LIKYASESIS GIPSRFSGSG SGTDFTLSIN SVESEDIADY YCQQNNNWPT

TFGAGTKLEL KRTVAAPSVF IFPPSDEQLK SGTASVVCLL NNFYPREAKV

QWKVDNALQS GNSQESVTEQ DSKDSTYSLS STLTLSKADY EKHKVYACEV

THQGLSSPVT KSFNRGA*]
Bold:              Albumin binding peptide
Underline:         Flexible Portion 1 (FP1)
Italics:           1203 Substrate
Double Underline:  Flexible Portion 2 (FP2)
Normal text:       C225

ABP-1203-C225 Heavy Chain DNA Sequence 2
[Signal Peptide (SEQ ID NO: 80)][C225 (SEQ ID NO: 14)]

(SEQ ID NO: 18)

[*atgtacaggatgcaactcctgtcttgcattgcactaagtcttgcacttgtcacgaattcg*][c aggtgcagctgaaacagagcggcccgggcctggtgcagccgagccagagcctgagcattacctg caccgtgagcggctttagcctgaccaactatggcgtgcattgggtgcgccagagcccgggcaaa ggcctggaatggctgggcgtgatttggagcggcggcaacaccgattataacaccccgtttacca gccgcctgagcattaacaaagataacagcaaaagccaggtgttttttaaaatgaacagcctgca aagcaacgataccgcgatttattattgcgcgcgcgcgctgacctattatgattatgaatttgcg tattggggccagggcacccctggtgaccgtgagcgcggctagcaccaagggcccatcggtcttcc ccctggcaccctcctccaagagcacctctggggggcacagcggccctgggctgcctggtcaagga ctacttccccgaaccggtgacggtgtcgtggaactcaggcgccctgaccagcggcgtgcacacc ttcccggctgtcctacagtcctcaggactctactccctcagcagcgtggtgaccgtgccctcca gcagcttgggcacccagacctacatctgcaacgtgaatcacaagcccagcaacaccaaggtgga caagaaagttgagcccaaatcttgtgacaaaactcacacatgcccaccgtgcccagcacctgaa ctcctggggggaccgtcagtcttcctcttccccccaaaacccaaggacaccctcatgatctccc ggaccccctgaggtcacatgcgtggtggtggacgtgagccacgaagaccctgaggtcaagttcaa ctggtacgtggacggcgtggaggtgcataatgccaagacaaagccgcgggaggagcagtacaac agcacgtaccgtgtggtcagcgtcctcaccgtcctgcaccaggactggctgaatggcaaggagt acaagtgcaaggtctccaacaaagccctcccagcccccatcgagaaaaccatctccaaagccaa agggcagccccgagaaccacaggtgtacaccctgcccccatcccgggatgaactgaccaagaac caggtcagcctgacctgcctggtcaaaggcttctatcccagcgacatcgccgtggagtgggaga gcaatgggcagccggagaacaactacaagaccacgcctcccgtgctggactccgacggctcctt cttcctctacagcaagctcaccgtggacaagagcaggtggcagcaggggaacgtcttctcatgc -continued

```
tccgtgatgcatgaggctctgcacaaccactacacgcagaagagcctctccctgtctccgggta aatga]
```
Bold and Italics: Signal peptide
Normal text:     C225

ABP-1203-C225 Heavy Chain Amino Acid Sequence 2
[Signal Peptide (SEQ ID NO: 81)][C225 (SEQ ID NO: 15)]

(SEQ ID NO: 19)

[*MYRMQLLSCI ALSLALVTNS*][QVQLKQSGPG LVQPSQSLSI TCTVSGFSLT

NYGVHWVRQS PGKGLEWLGV IWSGGNTDYN TPFTSRLSIN KDNSKSQVFF

KMNSLQSNDT AIYYCARALT YYDYEFAYWG QGTLVTVSAA STKGPSVFPL

APSSKSTSGG TAALGCLVKD YFPEPVTVSW NSGALTSGVH TFPAVLQSSG

LYSLSSVVTV PSSSLGTQTY ICNVNHKPSN TKVDKKVEPK SCDKTHTCPP

CPAPELLGGP SVFLFPPKPK DTLMISRTPE VTCVVVDVSH EDPEVKFNWY

VDGVEVHNAK TKPREEQYNS TYRVVSVLTV LHQDWLNGKE YKCKVSNKAL

PAPIEKTISK AKGQPREPQV YTLPPSRDEL TKNQVSLTCL VKGFYPSDIA

VEWESNGQPE NNYKTTPPVL DSDGSFFLYS KLTVDKSRWQ QGNVFSCSVM

HEALHNHYTQ KSLSLSPGK*]

Bold and Italics: Signal peptide
Normal text:     C225

ABP-1203-C225 Light Chain DNA Sequence 2
[Signal peptide (SEQ ID NO: 80)][AEP (SEQ ID NO: 74)][FP1 (SEQ ID NO: 75)][Substrate 1203 SEQ ID N: 76)][FP2 (SEQ ID NO: 77)][C225 (SEQ ID NO: 14)]

(SEQ ID NO: 20)

[atgtacaggatgcaactcctgtcttgcattgcactaagtcttgcacttgtcacgaattcg][c agagactgatggaggacatctgcctgccgagatggggatgcctgtgggaagacgacttc][ggc tcgagcggtggcagcggtggctctggtggatccggt][*actggccgtggtccaagctgggtt*]

[ggcggtacc][cagatcttgctgacccagagcccggtgattctgagcgtgagcccgggcgaacg tgtgagctttagctgccgcgcgagccagagcattggcaccaacattcattggtatcagcagcgc accaacggcagcccgcgcctgctgattaaatatgcgagcgaaagcattagcggcattccgagcc gctttagcggcagcggcagcggcaccgattttacccctgagcattaacagcgtggaaagcgaaga tattgcggattattattgccagcagaacaacaactggccgaccacctttggcgcgggcaccaaa ctggaactgaaacgtacggtggctgcaccatctgtcttcatcttcccgccatctgatgagcagt tgaaatctggaactgcctctgttgtgtgcctgctgaataacttctatcccagagaggccaaagt acagtggaaggtggataacgccctccaatcgggtaactcccaggagagtgtcacagagcaggac agcaaggacagcacctacagcctcagcagcaccctgacgctgagcaaagcagactacgagaaac acaaagtctacgcctgcgaagtcacccatcagggcctgagctcgcccgtcacaaagagcttcaa caggggagcgtag]

Bold and Italics: Signal peptide
Bold:             Albumin binding peptide
Underline:        Flexible Portion 1 (FP1)
Italics:          1203 Substrate
Double Underline: Flexible Portion 2 (FP2)
Normal text:      C225

ABP-1203-C225 Light Chain Amino Acid Sequence 2
[Signal peptide (SEQ ID NO: 81)][ABP][FP1][Substrate 1203][FP2][C225 (SEQ ID NO: 15)]

(SEQ ID NO: 21)

[*MYRMQLLSCI ALSLALVTNS*][QRLMEDICLP RWGCLWEDDF][GSSGGSGGSG

GSG][*TGRGPSW V*][GGT][QILLTQ SPVILSVSPG ERVSFSCRAS QSIGTNIHWY

QQRTNGSPRL LIKYASESIS GIPSRFSGSG SGTDFTLSIN SVESEDIADY

```
                                   -continued
YCQQNNNWPT TFGAGTKLEL KRTVAAPSVF IFPPSDEQLK SGTASVVCLL

NNFYPREAKV QWKVDNALQS GNSQESVTEQ DSKDSTYSLS STLTLSKADY

EKHKVYACEV THQGLSSPVT KSFNRGA*]
Bold and Italics: Signal peptide
Bold:             Albumin binding peptide
Underline:        Flexible Portion 1 (FP1)
Italics:          1203 Substrate
Double Underline: Flexible Portion 2 (FP2)
Normal text:      C225
```

Figure 2:
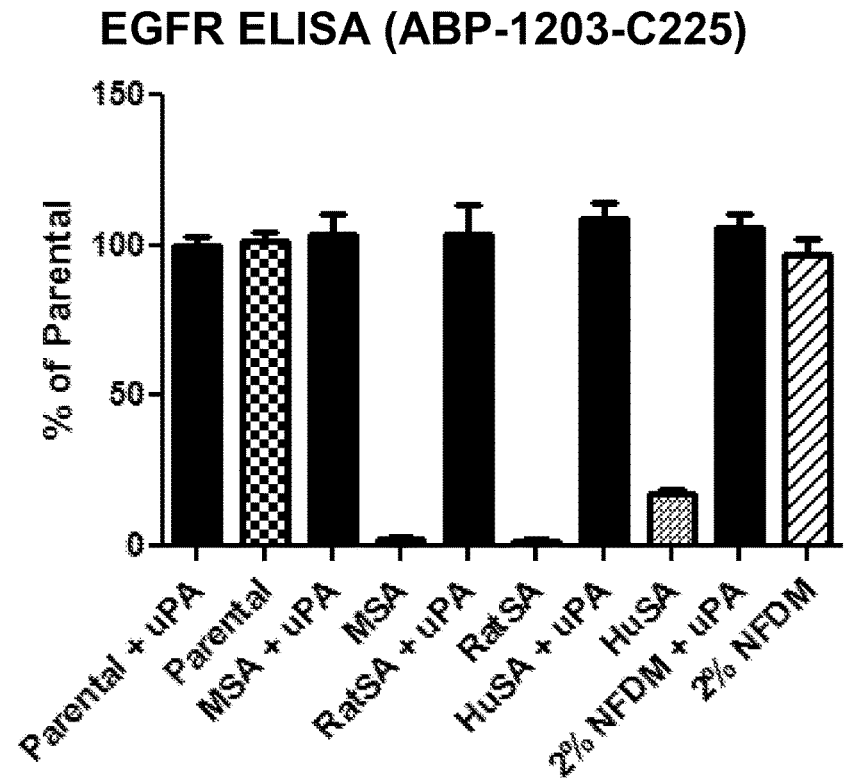
FIG. 2 is a graph depicting the ability of an activatable antibody referred to as activatable antibody ABP-1203-C225, to bind to EGFR antigen under various conditions as compared to ability of the C225 parental antibody to bind to EGFR antigen.

Example 2. Affect of Serum Albumin on Binding of a BP-Activatable Antibody to its Target A test to compare the abilities of activatable antibody ABP-1203-C225 and C225 parental antibody to bind to EGFR antigen was conducted under various conditions to assess the ability of albumin to block such binding by the activatable antibody. Results are depicted in FIG. 2. Briefly, the parental antibody (C225) or the activatable antibody ABP-1203-C225 (100 nM) was incubated with or without the human protease, urokinase plasminogen activator (uPA; 10 μg/ml, R&D Systems) at 37° C. O/N in uPA digestion buffer (50 mM Tris, pH 7.4, 100 mM NaCl, 1 mM EDTA, and 0.01% Tween-20). Activatable antibody treated with uPA was diluted in binding buffer (TBS (50 mM Tris-HCl, pH 7.4, 150 mM NaCl) plus 2 mM $CaCl_2$) that included 50 mg/ml of various serum albumins (mouse serum albumin (MSA), rat serum albumin (RatSA), or human serum albumin (HuSA) (each being available from Sigma) as indicated, or with non-fat dry milk (NFDM) as a negative control. The samples were then subjected to an ELISA (1 h at room temperature) on plates pre-coated with human EGFR (the 96-well plate was coated with 1 ug/ml EGFR-hFc (R&D Systems) in TBS plus 2 mM $CaCl_2$ at 4° C. overnight, blocked with 2% non-fat dry milk. The samples were added to each well and incubated at room temperature for 1 h, then detected with HRP-conjugated goat-anti-human F(ab)₂ antibodies) (available from R&D Systems). The ELISA results showed that the EGFR-binding ability of the parental antibody was not affected by uPA treatment. A similar level of EGFR binding was shown by ABP-1203-C225 that had been incubated with non-fat dry milk, regardless of whether ABP-1203-C225 had been treated with uPA. These results indicate both that the ABP peptide itself was not sufficient for blocking EGFR binding, and that milk did not contain an effective non-binding steric moiety (NB). In contrast, each of the albumin proteins (from mouse, rat, or human) significantly reduced the ability of activatable antibody ABP-1203-C225 to bind EGFR. However, pre-digestion of the ABP-1203-C225 with uPA restored EGFR binding of the activated protein, indicating that the ABP-1203-C225 protein was activated by digestion of the CL linker.

Figure 3:
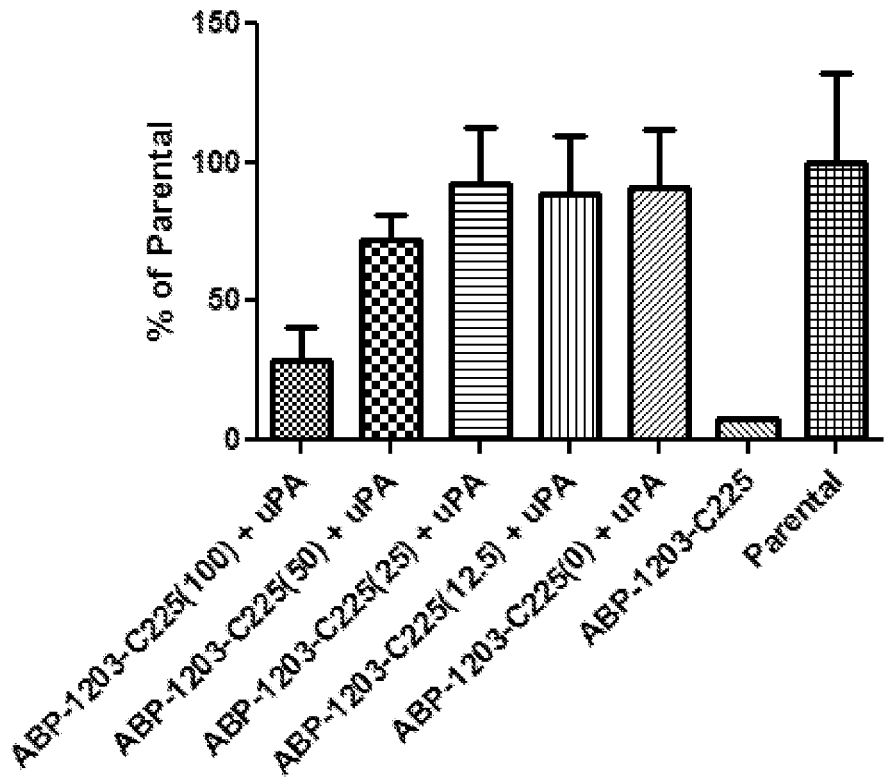
FIG. 3 is a graph depicting the ability of the activatable antibody ABP-1203-C225 to be digested by uPA protease in the presence of a concentration of albumin sufficient to block EGFR binding.

The ability of activatable antibody ABP-1203-C225 to be digested by uPA protease in the presence of a concentration of albumin sufficient to block EGFR binding is shown in FIG. 3. Activatable antibody ABP-1203-C225 was digested with uPA (10 μg/ml) in the presence of a range of concentrations of mouse serum albumin (0-100 mg/ml) in uPA digestion buffer at 37° C. overnight. The digested antibody was then diluted in binding buffer including 50 mg/ml mouse serum albumin and subjected to EGFR ELISA (1 h at room temperature). The results showed that uPA was able to activate ABP-1203-C225 for EGFR binding in the presence of albumin concentrations up to 50 mg/mL, a concentration similar to that normally found in mouse serum. At a higher concentration of albumin, uPA activation was still observed, but was partially inhibited. This may result from a steric block at high albumin concentrations or from contaminants in the albumin preparation.

Figure 4:
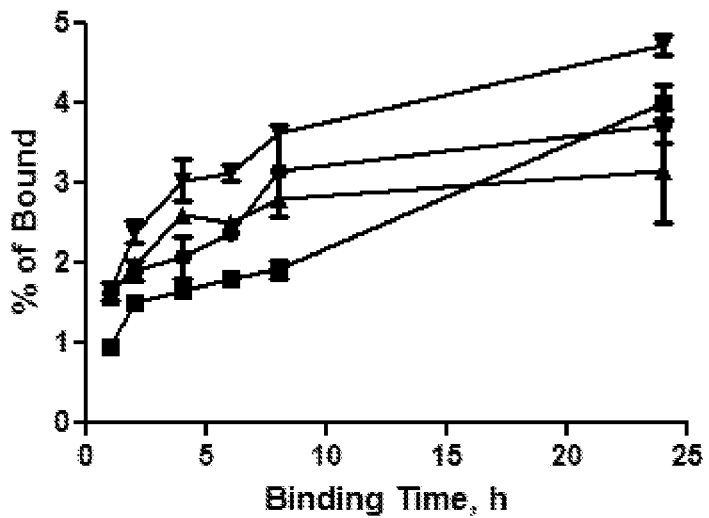
FIG. 4 is a graph depicting that the activatable antibody ABP-1203-C225 exhibited less than 5% of parental antibody binding in the presence of mouse or rat serum, albumin, and protease inhibitors.
Figure 5:
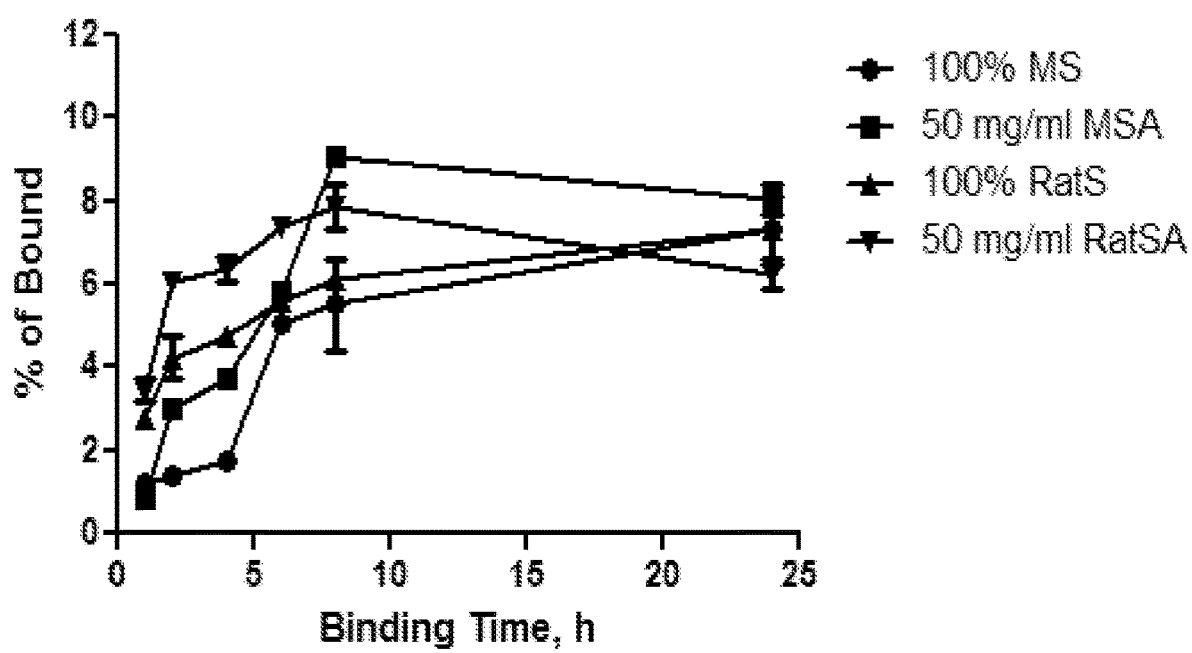
FIG. 5 is a graph depicting that the activatable antibody ABP-1203-C225 exhibited less than 10% of parental antibody binding in the presence of mouse or rat serum and albumin.

The masking efficiency of albumin was also tested over time by incubating activatable antibody ABP-1203-C225 in the presence of mouse or rat serum (available from Innovative Research) or purified albumin (50 mg/mL) on an EGFR-pre-coated ELISA plate for 24 h at 37° C. in the presence of protease inhibitors (complete, EDTA-free protease inhibitors cocktail tablet (Roche Cat #04693159001)). FIG. 4 shows that ABP-1203-C225 exhibits less than 5% of parental antibody binding under these conditions. This experiment was also carried out in the absence of protease inhibitors, resulting in ABP-1203-C225 exhibiting less than 10% of parental antibody binding over 24 h at 37° C. (FIG. 5).

Together, these results indicate that activatable antibody ABP-1203-C225 protein can be blocked from binding EGFR antigen in the presence of physiological concentrations of albumin (or albumin-containing serum), and that the activatable antibody can be activated by a specific protease, uPA, in the presence of albumin.

The results suggest that BP-activatable antibodies can be used to treat patients in which specific proteins are up-regulated at sites of disease. Upon administration to a patient, a BP-activatable antibody recruits a non-binding steric moiety, e.g., an ABP-activatable antibody recruits albumin. In the circulation and in non-target tissues, the recruited non-binding steric moiety blocks the ability of the activatable antibody to bind to its target antigen. However, at diseased sites where specific proteases (such as uPA) are up-regulated, the cleavable linker attaching the BP to the antibody can be digested, releasing the NB-bound BP, and resulting in an active antibody that binds to its target antigen.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

<160> NUMBER OF SEQ ID NOS: 81

<210> SEQ ID NO 1
<211> LENGTH: 20

<212> TYPE: PRT
<213> ORGANISM: Artificial Sequence
<220> FEATURE:
<223> OTHER INFORMATION: chemically synthesized

<400> SEQUENCE: 1

Gln Arg Leu Met Glu Asp Ile Cys Leu Pro Arg Trp Gly Cys Leu Trp
1               5                   10                  15

Glu Asp Asp Phe
            20

<210> SEQ ID NO 2
<211> LENGTH: 22
<212> TYPE: PRT
<213> ORGANISM: Artificial Sequence
<220> FEATURE:
<223> OTHER INFORMATION: chemically synthesized

<400> SEQUENCE: 2

Gly Ser Ser Gly Gly Ser Gly Gly Ser Gly Gly Ser Gly Gly Gly Ser
1               5                   10                  15

Gly Gly Gly Ser Gly Gly
            20

<210> SEQ ID NO 3
<211> LENGTH: 8
<212> TYPE: PRT
<213> ORGANISM: Artificial Sequence
<220> FEATURE:
<223> OTHER INFORMATION: chemically synthesized

<400> SEQUENCE: 3

Thr Gly Arg Gly Pro Ser Trp Val
1               5

<210> SEQ ID NO 4
<211> LENGTH: 45
<212> TYPE: PRT
<213> ORGANISM: Artificial Sequence
<220> FEATURE:
<223> OTHER INFORMATION: chemically synthesized

<400> SEQUENCE: 4

Gln Arg Leu Met Glu Asp Ile Cys Leu Pro Arg Trp Gly Cys Leu Trp
1               5                   10                  15

Glu Asp Asp Phe Gly Ser Ser Gly Gly Ser Gly Gly Ser Gly Gly Ser
            20                  25                  30

Gly Thr Gly Arg Gly Pro Ser Trp Val Gly Gly Thr Gln
            35                  40                  45

<210> SEQ ID NO 5
<211> LENGTH: 5
<212> TYPE: PRT
<213> ORGANISM: Artificial Sequence
<220> FEATURE:
<223> OTHER INFORMATION: chemically synthesized

<400> SEQUENCE: 5

Gly Ser Gly Gly Ser
1               5

<210> SEQ ID NO 6
<211> LENGTH: 4
<212> TYPE: PRT
<213> ORGANISM: Artificial Sequence

```
<220> FEATURE:
<223> OTHER INFORMATION: chemically synthesized

<400> SEQUENCE: 6

Gly Gly Gly Ser
1

<210> SEQ ID NO 7
<211> LENGTH: 4
<212> TYPE: PRT
<213> ORGANISM: Artificial Sequence
<220> FEATURE:
<223> OTHER INFORMATION: chemically synthesized

<400> SEQUENCE: 7

Gly Gly Ser Gly
1

<210> SEQ ID NO 8
<211> LENGTH: 5
<212> TYPE: PRT
<213> ORGANISM: Artificial Sequence
<220> FEATURE:
<223> OTHER INFORMATION: chemically synthesized

<400> SEQUENCE: 8

Gly Gly Ser Gly Gly
1               5

<210> SEQ ID NO 9
<211> LENGTH: 5
<212> TYPE: PRT
<213> ORGANISM: Artificial Sequence
<220> FEATURE:
<223> OTHER INFORMATION: chemically synthesized

<400> SEQUENCE: 9

Gly Ser Gly Ser Gly
1               5

<210> SEQ ID NO 10
<211> LENGTH: 5
<212> TYPE: PRT
<213> ORGANISM: Artificial Sequence
<220> FEATURE:
<223> OTHER INFORMATION: chemically synthesized

<400> SEQUENCE: 10

Gly Ser Gly Gly Gly
1               5

<210> SEQ ID NO 11
<211> LENGTH: 5
<212> TYPE: PRT
<213> ORGANISM: Artificial Sequence
<220> FEATURE:
<223> OTHER INFORMATION: chemically synthesized

<400> SEQUENCE: 11

Gly Gly Gly Ser Gly
1               5

<210> SEQ ID NO 12
<211> LENGTH: 5
<212> TYPE: PRT
<213> ORGANISM: Artificial Sequence
<220> FEATURE:
```

<223> OTHER INFORMATION: chemically synthesized

<400> SEQUENCE: 12

Gly Ser Ser Ser Gly
1               5

<210> SEQ ID NO 13
<211> LENGTH: 5
<212> TYPE: PRT
<213> ORGANISM: Artificial Sequence
<220> FEATURE:
<223> OTHER INFORMATION: chemically synthesized

<400> SEQUENCE: 13

Glu Gly Gly Gly Ser
1               5

<210> SEQ ID NO 14
<211> LENGTH: 1350
<212> TYPE: DNA
<213> ORGANISM: Artificial Sequence
<220> FEATURE:
<223> OTHER INFORMATION: chemically synthesized

<400> SEQUENCE: 14

```
caggtgcagc tgaaacagag cggcccgggc ctggtgcagc cgagccagag cctgagcatt      60
acctgcaccg tgagcggctt tagcctgacc aactatggcg tgcattgggt gcgccagagc     120
ccgggcaaag cctggaatg gctgggcgtg atttggagcg gcggcaacac cgattataac     180
accccgttta ccagccgcct gagcattaac aaagataaca gcaaaagcca ggtgtttttt    240
aaaatgaaca gcctgcaaag caacgatacc gcgatttatt attgcgcgcg cgcgctgacc    300
tattatgatt atgaatttgc gtattggggc cagggcaccc tggtgaccgt gagcgcggct    360
agcaccaagg gcccatcggt cttccccctg gcaccctcct ccaagagcac ctctggggc     420
acagcggccc tgggctgcct ggtcaaggac tacttcccg aaccggtgac ggtgtcgtgg    480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
atctgcaacg tgaatcacaa gcccagcaac accaaggtgg acaagaaagt tgagcccaaa   660
tcttgtgaca aaactcacac atgcccaccg tgcccagcac ctgaactcct ggggggaccg   720
tcagtcttcc tcttcccccc aaaacccaag gacaccctca tgatctcccg gacccctgag   780
gtcacatgcg tggtggtgga cgtgagccac gaagaccctg aggtcaagtt caactggtac   840
gtggacggcg tggaggtgca taatgccaag acaaagccgc gggaggagca gtacaacagc   900
acgtaccgtg tggtcagcgt cctcaccgtc ctgcaccagg actggctgaa tggcaaggag   960
tacaagtgca aggtctccaa caaagccctc ccagcccca tcgagaaaac catctccaaa   1020
gccaaagggc agccccgaga accacaggtg tacaccctgc ccccatcccg ggatgaactg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaatga                                    1350
```

<210> SEQ ID NO 15
<211> LENGTH: 449

<212> TYPE: PRT
<213> ORGANISM: Artificial Sequence
<220> FEATURE:
<223> OTHER INFORMATION: chemically synthesized

<400> SEQUENCE: 15

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

Ser Asn Gly Gln Pro Glu Asn Asn Tyr Lys Thr Thr Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 16
<211> LENGTH: 774
<212> TYPE: DNA
<213> ORGANISM: Artificial Sequence
<220> FEATURE:
<223> OTHER INFORMATION: chemically synthesized

<400> SEQUENCE: 16
cagagactga tggaggacat ctgcctgccg agatggggat gcctgtggga agacgacttc      60
ggctcgagcg gtggcagcgg tggctctggt ggatccggta ctggccgtgg tccaagctgg     120
gttggcggta cccagatctt gctgacccag agcccggtga ttctgagcgt gagcccgggc     180
gaacgtgtga gctttagctg ccgcgcgagc cagagcattg gcaccaacat tcattggtat     240
cagcagcgca ccaacggcag cccgcgcctg ctgattaaat atgcgagcga aagcattagc     300
ggcattccga ccgctttag cggcagcggc agcggcaccg attttaccct gagcattaac     360
agcgtggaaa gcgaagatat tgcggattat tattgccagc agaacaacaa ctggccgacc     420
acctttggcg cgggcaccaa actggaactg aaacgtacgg tggctgcacc atctgtcttc     480
atcttcccgc catctgatga gcagttgaaa tctggaactg cctctgttgt gtgcctgctg     540
aataacttct atcccagaga ggccaaagta cagtggaagg tggataacgc cctccaatcg     600
ggtaactccc aggagagtgt cacagagcag gacagcaagg acagcaccta cagcctcagc     660
agcaccctga cgctgagcaa agcagactac gagaaacaca agtctacgc ctgcgaagtc      720 acccatcagg gcctgagctc gcccgtcaca aagagcttca caggggagc gtag            774

<210> SEQ ID NO 17
<211> LENGTH: 257
<212> TYPE: PRT
<213> ORGANISM: Artificial Sequence
<220> FEATURE:
<223> OTHER INFORMATION: chemically synthesized

<400> SEQUENCE: 17

Gln Arg Leu Met Glu Asp Ile Cys Leu Pro Arg Trp Gly Cys Leu Trp
1               5                   10                  15

Glu Asp Asp Phe Gly Ser Ser Gly Gly Ser Gly Gly Ser Gly Gly Ser
            20                  25                  30

Gly Thr Gly Arg Gly Pro Ser Trp Val Gly Gly Thr Gln Ile Leu Leu
        35                  40                  45

Thr Gln Ser Pro Val Ile Leu Ser Val Ser Pro Gly Glu Arg Val Ser
    50                  55                  60

Phe Ser Cys Arg Ala Ser Gln Ser Ile Gly Thr Asn Ile His Trp Tyr
65                  70                  75                  80

Gln Gln Arg Thr Asn Gly Ser Pro Arg Leu Leu Ile Lys Tyr Ala Ser
                85                  90                  95

Glu Ser Ile Ser Gly Ile Pro Ser Arg Phe Ser Gly Ser Gly Ser Gly

```
            100                 105                 110
Thr Asp Phe Thr Leu Ser Ile Asn Ser Val Glu Ser Glu Asp Ile Ala
        115                 120                 125
Asp Tyr Tyr Cys Gln Gln Asn Asn Asn Trp Pro Thr Thr Phe Gly Ala
        130                 135                 140
Gly Thr Lys Leu Glu Leu Lys Arg Thr Val Ala Ala Pro Ser Val Phe
145                 150                 155                 160
Ile Phe Pro Pro Ser Asp Glu Gln Leu Lys Ser Gly Thr Ala Ser Val
                165                 170                 175
Val Cys Leu Leu Asn Asn Phe Tyr Pro Arg Glu Ala Lys Val Gln Trp
                180                 185                 190
Lys Val Asp Asn Ala Leu Gln Ser Gly Asn Ser Gln Glu Ser Val Thr
                195                 200                 205
Glu Gln Asp Ser Lys Asp Ser Thr Tyr Ser Leu Ser Ser Thr Leu Thr
        210                 215                 220
Leu Ser Lys Ala Asp Tyr Glu Lys His Lys Val Tyr Ala Cys Glu Val
225                 230                 235                 240
Thr His Gln Gly Leu Ser Ser Pro Val Thr Lys Ser Phe Asn Arg Gly
                245                 250                 255
Ala
```

<210> SEQ ID NO 18
<211> LENGTH: 1410
<212> TYPE: DNA
<213> ORGANISM: Artificial Sequence
<220> FEATURE:
<223> OTHER INFORMATION: chemically synthesized

<400> SEQUENCE: 18

```
atgtacagga tgcaactcct gtcttgcatt gcactaagtc ttgcacttgt cacgaattcg      60
caggtgcagc tgaaacagag cggcccgggc ctggtgcagc cgagccagag cctgagcatt     120
acctgcaccg tgagcggctt tagcctgacc aactatggcg tgcattgggt gcgccagagc     180
ccgggcaaag gcctggaatg gctgggcgtg atttggagcg gcggcaacac cgattataac     240
accccgttta ccagccgcct gagcattaac aaagataaca gcaaaagcca ggtgtttttt     300
aaaatgaaca gcctgcaaag caacgatacc gcgatttatt attgcgcgcg cgcgctgacc     360
tattatgatt atgaatttgc gtattggggc cagggcaccc tggtgaccgt gagcgcggct     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttccccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggatgaactg    1140
```

```
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga                                     1410
```

<210> SEQ ID NO 19
<211> LENGTH: 469
<212> TYPE: PRT
<213> ORGANISM: Artificial Sequence
<220> FEATURE:
<223> OTHER INFORMATION: chemically synthesized

<400> SEQUENCE: 19

```
Met Tyr Arg Met Gln Leu Leu Ser Cys Ile Ala Leu Ser Leu Ala Leu
1               5                   10                  15

Val Thr Asn Ser Gln Val Gln Leu Lys Gln Ser Gly Pro Gly Leu Val
            20                  25                  30

Gln Pro Ser Gln Ser Leu Ser Ile Thr Cys Thr Val Ser Gly Phe Ser
        35                  40                  45

Leu Thr Asn Tyr Gly Val His Trp Val Arg Gln Ser Pro Gly Lys Gly
    50                  55                  60

Leu Glu Trp Leu Gly Val Ile Trp Ser Gly Gly Asn Thr Asp Tyr Asn
65                  70                  75                  80

Thr Pro Phe Thr Ser Arg Leu Ser Ile Asn Lys Asp Asn Ser Lys Ser
                85                  90                  95

Gln Val Phe Phe Lys Met Asn Ser Leu Gln Ser Asn Asp Thr Ala Ile
            100                 105                 110

Tyr Tyr Cys Ala Arg Ala Leu Thr Tyr Tyr Asp Tyr Glu Phe Ala Tyr
        115                 120                 125

Trp Gly Gln Gly Thr Leu Val Thr Val Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320
```

```
Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 20
<211> LENGTH: 834
<212> TYPE: DNA
<213> ORGANISM: Artificial Sequence
<220> FEATURE:
<223> OTHER INFORMATION: chemically synthesized

<400> SEQUENCE: 20
atgtacagga tgcaactcct gtcttgcatt gcactaagtc ttgcacttgt cacgaattcg      60
cagagactga tggaggacat ctgcctgccg agatggggat gcctgtggga agacgacttc    120
ggctcgagcg gtggcagcgg tggctctggt ggatccggta ctggccgtgg tccaagctgg    180
gttggcggta cccagatctt gctgacccag agcccggtga ttctgagcgt gagcccgggc    240
gaacgtgtga gctttagctg ccgcgcgagc cagagcattg gcaccaacat tcattggtat    300
cagcagcgca ccaacggcag cccgcgcctg ctgattaaat atgcgagcga aagcattagc    360
ggcattccga ccgctttag cggcagcggc agcggcaccg ttttaccct gagcattaac    420 agcgtggaaa gcgaagatat tgcggattat tattgccagc agaacaacaa ctggccgacc    480
acctttggcg cgggcaccaa actggaactg aaacgtacgg tggctgcacc atctgtcttc    540
atcttcccgc catctgatga gcagttgaaa tctggaactg cctctgttgt gtgcctgctg    600
aataacttct atcccagaga ggccaaagta cagtggaagg tggataacgc cctccaatcg    660
ggtaactccc aggagagtgt cacagagcag gacagcaagg acagcaccta cagcctcagc    720
agcaccctga cgctgagcaa agcagactac gagaaacaca agtctacgc ctgcgaagtc    780 acccatcagg gcctgagctc gcccgtcaca aagagcttca caggggagc gtag    834

<210> SEQ ID NO 21
<211> LENGTH: 277
<212> TYPE: PRT
<213> ORGANISM: Artificial Sequence
<220> FEATURE:
<223> OTHER INFORMATION: chemically synthesized

<400> SEQUENCE: 21
```

```
Met Tyr Arg Met Gln Leu Leu Ser Cys Ile Ala Leu Ser Leu Ala Leu
1               5                   10                  15

Val Thr Asn Ser Gln Arg Leu Met Glu Asp Ile Cys Leu Pro Arg Trp
            20                  25                  30

Gly Cys Leu Trp Glu Asp Asp Phe Gly Ser Ser Gly Ser Gly Gly Gly
        35                  40                  45

Ser Gly Gly Ser Gly Thr Gly Arg Gly Pro Ser Trp Val Gly Gly Thr
    50                  55                  60

Gln Ile Leu Leu Thr Gln Ser Pro Val Ile Leu Ser Val Ser Pro Gly
65                  70                  75                  80

Glu Arg Val Ser Phe Ser Cys Arg Ala Ser Gln Ser Ile Gly Thr Asn
                85                  90                  95

Ile His Trp Tyr Gln Gln Arg Thr Asn Gly Ser Pro Arg Leu Leu Ile
            100                 105                 110

Lys Tyr Ala Ser Glu Ser Ile Ser Gly Ile Pro Ser Arg Phe Ser Gly
        115                 120                 125

Ser Gly Ser Gly Thr Asp Phe Thr Leu Ser Ile Asn Ser Val Glu Ser
    130                 135                 140

Glu Asp Ile Ala Asp Tyr Tyr Cys Gln Gln Asn Asn Asn Trp Pro Thr
145                 150                 155                 160

Thr Phe Gly Ala Gly Thr Lys Leu Glu Leu Lys Arg Thr Val Ala Ala
                165                 170                 175

Pro Ser Val Phe Ile Phe Pro Pro Ser Asp Glu Gln Leu Lys Ser Gly
            180                 185                 190

Thr Ala Ser Val Val Cys Leu Leu Asn Asn Phe Tyr Pro Arg Glu Ala
        195                 200                 205

Lys Val Gln Trp Lys Val Asp Asn Ala Leu Gln Ser Gly Asn Ser Gln
    210                 215                 220

Glu Ser Val Thr Glu Gln Asp Ser Lys Asp Ser Thr Tyr Ser Leu Ser
225                 230                 235                 240

Ser Thr Leu Thr Leu Ser Lys Ala Asp Tyr Glu Lys His Lys Val Tyr
                245                 250                 255

Ala Cys Glu Val Thr His Gln Gly Leu Ser Ser Pro Val Thr Lys Ser
            260                 265                 270

Phe Asn Arg Gly Ala
        275

<210> SEQ ID NO 22
<211> LENGTH: 8
<212> TYPE: PRT
<213> ORGANISM: Artificial Sequence
<220> FEATURE:
<223> OTHER INFORMATION: chemically synthesized

<400> SEQUENCE: 22

Ser Ala Arg Gly Pro Ser Arg Trp
1               5

<210> SEQ ID NO 23
<211> LENGTH: 8
<212> TYPE: PRT
<213> ORGANISM: Artificial Sequence
<220> FEATURE:
<223> OTHER INFORMATION: chemically synthesized

<400> SEQUENCE: 23

Thr Ala Arg Gly Pro Ser Phe Lys
1               5
```

```
<210> SEQ ID NO 24
<211> LENGTH: 7
<212> TYPE: PRT
<213> ORGANISM: Artificial Sequence
<220> FEATURE:
<223> OTHER INFORMATION: chemically synthesized

<400> SEQUENCE: 24

Thr Ala Arg Gly Pro Ser Trp
1               5

<210> SEQ ID NO 25
<211> LENGTH: 8
<212> TYPE: PRT
<213> ORGANISM: Artificial Sequence
<220> FEATURE:
<223> OTHER INFORMATION: chemically synthesized

<400> SEQUENCE: 25

Leu Ser Gly Arg Ser Asp Asn His
1               5

<210> SEQ ID NO 26
<211> LENGTH: 8
<212> TYPE: PRT
<213> ORGANISM: Artificial Sequence
<220> FEATURE:
<223> OTHER INFORMATION: chemically synthesized

<400> SEQUENCE: 26

Gly Gly Trp His Thr Gly Arg Asn
1               5

<210> SEQ ID NO 27
<211> LENGTH: 8
<212> TYPE: PRT
<213> ORGANISM: Artificial Sequence
<220> FEATURE:
<223> OTHER INFORMATION: chemically synthesized

<400> SEQUENCE: 27

His Thr Gly Arg Ser Gly Ala Leu
1               5

<210> SEQ ID NO 28
<211> LENGTH: 8
<212> TYPE: PRT
<213> ORGANISM: Artificial Sequence
<220> FEATURE:
<223> OTHER INFORMATION: chemically synthesized

<400> SEQUENCE: 28

Pro Leu Thr Gly Arg Ser Gly Gly
1               5

<210> SEQ ID NO 29
<211> LENGTH: 7
<212> TYPE: PRT
<213> ORGANISM: Artificial Sequence
<220> FEATURE:
<223> OTHER INFORMATION: chemically synthesized

<400> SEQUENCE: 29

Leu Thr Gly Arg Ser Gly Ala
1               5
```

```
<210> SEQ ID NO 30
<211> LENGTH: 8
<212> TYPE: PRT
<213> ORGANISM: Artificial Sequence
<220> FEATURE:
<223> OTHER INFORMATION: chemically synthesized

<400> SEQUENCE: 30

Ala Ala Arg Gly Pro Ala Ile His
1               5

<210> SEQ ID NO 31
<211> LENGTH: 8
<212> TYPE: PRT
<213> ORGANISM: Artificial Sequence
<220> FEATURE:
<223> OTHER INFORMATION: chemically synthesized

<400> SEQUENCE: 31

Arg Gly Pro Ala Phe Asn Pro Met
1               5

<210> SEQ ID NO 32
<211> LENGTH: 8
<212> TYPE: PRT
<213> ORGANISM: Artificial Sequence
<220> FEATURE:
<223> OTHER INFORMATION: chemically synthesized

<400> SEQUENCE: 32

Ser Ser Arg Gly Pro Ala Tyr Leu
1               5

<210> SEQ ID NO 33
<211> LENGTH: 8
<212> TYPE: PRT
<213> ORGANISM: Artificial Sequence
<220> FEATURE:
<223> OTHER INFORMATION: chemically synthesized

<400> SEQUENCE: 33

Arg Gly Pro Ala Thr Pro Ile Met
1               5

<210> SEQ ID NO 34
<211> LENGTH: 4
<212> TYPE: PRT
<213> ORGANISM: Artificial Sequence
<220> FEATURE:
<223> OTHER INFORMATION: chemically synthesized

<400> SEQUENCE: 34

Arg Gly Pro Ala
1

<210> SEQ ID NO 35
<211> LENGTH: 4
<212> TYPE: PRT
<213> ORGANISM: Artificial Sequence
<220> FEATURE:
<223> OTHER INFORMATION: chemically synthesized

<400> SEQUENCE: 35

Ala Ala Asn Leu
1
```

```
<210> SEQ ID NO 36
<211> LENGTH: 4
<212> TYPE: PRT
<213> ORGANISM: Artificial Sequence
<220> FEATURE:
<223> OTHER INFORMATION: chemically synthesized

<400> SEQUENCE: 36

Pro Thr Asn Leu
1

<210> SEQ ID NO 37
<211> LENGTH: 6
<212> TYPE: PRT
<213> ORGANISM: Artificial Sequence
<220> FEATURE:
<223> OTHER INFORMATION: chemically synthesized

<400> SEQUENCE: 37

Gln Gly Gln Ser Gly Gln
1               5

<210> SEQ ID NO 38
<211> LENGTH: 10
<212> TYPE: PRT
<213> ORGANISM: Artificial Sequence
<220> FEATURE:
<223> OTHER INFORMATION: chemically synthesized

<400> SEQUENCE: 38

Gly Gly Gln Pro Ser Gly Met Trp Gly Trp
1               5                   10

<210> SEQ ID NO 39
<211> LENGTH: 10
<212> TYPE: PRT
<213> ORGANISM: Artificial Sequence
<220> FEATURE:
<223> OTHER INFORMATION: chemically synthesized

<400> SEQUENCE: 39

Phe Pro Arg Pro Leu Gly Ile Thr Gly Leu
1               5                   10

<210> SEQ ID NO 40
<211> LENGTH: 10
<212> TYPE: PRT
<213> ORGANISM: Artificial Sequence
<220> FEATURE:
<223> OTHER INFORMATION: chemically synthesized

<400> SEQUENCE: 40

Val His Met Pro Leu Gly Phe Leu Gly Pro
1               5                   10

<210> SEQ ID NO 41
<211> LENGTH: 8
<212> TYPE: PRT
<213> ORGANISM: Artificial Sequence
<220> FEATURE:
<223> OTHER INFORMATION: chemically synthesized

<400> SEQUENCE: 41

Ser Pro Leu Thr Gly Arg Ser Gly
1               5

<210> SEQ ID NO 42
```

```
<211> LENGTH: 8
<212> TYPE: PRT
<213> ORGANISM: Artificial Sequence
<220> FEATURE:
<223> OTHER INFORMATION: chemically synthesized

<400> SEQUENCE: 42

Ser Ala Gly Phe Ser Leu Pro Ala
1               5

<210> SEQ ID NO 43
<211> LENGTH: 9
<212> TYPE: PRT
<213> ORGANISM: Artificial Sequence
<220> FEATURE:
<223> OTHER INFORMATION: chemically synthesized

<400> SEQUENCE: 43

Leu Ala Pro Leu Gly Leu Gln Arg Arg
1               5

<210> SEQ ID NO 44
<211> LENGTH: 8
<212> TYPE: PRT
<213> ORGANISM: Artificial Sequence
<220> FEATURE:
<223> OTHER INFORMATION: chemically synthesized

<400> SEQUENCE: 44

Ser Gly Gly Pro Leu Gly Val Arg
1               5

<210> SEQ ID NO 45
<211> LENGTH: 4
<212> TYPE: PRT
<213> ORGANISM: Artificial Sequence
<220> FEATURE:
<223> OTHER INFORMATION: chemically synthesized

<400> SEQUENCE: 45

Pro Leu Gly Leu
1

<210> SEQ ID NO 46
<211> LENGTH: 8
<212> TYPE: PRT
<213> ORGANISM: Artificial Sequence
<220> FEATURE:
<223> OTHER INFORMATION: chemically synthesized

<400> SEQUENCE: 46

Pro Arg Phe Lys Ile Ile Gly Gly
1               5

<210> SEQ ID NO 47
<211> LENGTH: 8
<212> TYPE: PRT
<213> ORGANISM: Artificial Sequence
<220> FEATURE:
<223> OTHER INFORMATION: chemically synthesized

<400> SEQUENCE: 47

Pro Arg Phe Arg Ile Ile Gly Gly
1               5

<210> SEQ ID NO 48
<211> LENGTH: 9
```

```
<212> TYPE: PRT
<213> ORGANISM: Artificial Sequence
<220> FEATURE:
<223> OTHER INFORMATION: chemically synthesized

<400> SEQUENCE: 48

Ser Ser Arg His Arg Arg Ala Leu Asp
1               5

<210> SEQ ID NO 49
<211> LENGTH: 14
<212> TYPE: PRT
<213> ORGANISM: Artificial Sequence
<220> FEATURE:
<223> OTHER INFORMATION: chemically synthesized

<400> SEQUENCE: 49

Arg Lys Ser Ser Ile Ile Ile Arg Met Arg Asp Val Val Leu
1               5                   10

<210> SEQ ID NO 50
<211> LENGTH: 15
<212> TYPE: PRT
<213> ORGANISM: Artificial Sequence
<220> FEATURE:
<223> OTHER INFORMATION: chemically synthesized

<400> SEQUENCE: 50

Ser Ser Ser Phe Asp Lys Gly Lys Tyr Lys Lys Gly Asp Asp Ala
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: chemically synthesized

<400> SEQUENCE: 51

Ser Ser Ser Phe Asp Lys Gly Lys Tyr Lys Arg Gly Asp Asp Ala
1               5                   10                  15

<210> SEQ ID NO 52
<211> LENGTH: 4
<212> TYPE: PRT
<213> ORGANISM: Artificial Sequence
<220> FEATURE:
<223> OTHER INFORMATION: chemically synthesized

<400> SEQUENCE: 52

Ile Glu Gly Arg
1

<210> SEQ ID NO 53
<211> LENGTH: 4
<212> TYPE: PRT
<213> ORGANISM: Artificial Sequence
<220> FEATURE:
<223> OTHER INFORMATION: chemically synthesized

<400> SEQUENCE: 53

Ile Asp Gly Arg
1

<210> SEQ ID NO 54
<211> LENGTH: 7
<212> TYPE: PRT
```

```
<213> ORGANISM: Artificial Sequence
<220> FEATURE:
<223> OTHER INFORMATION: chemically synthesized

<400> SEQUENCE: 54

Gly Gly Ser Ile Asp Gly Arg
1               5

<210> SEQ ID NO 55
<211> LENGTH: 6
<212> TYPE: PRT
<213> ORGANISM: Artificial Sequence
<220> FEATURE:
<223> OTHER INFORMATION: chemically synthesized

<400> SEQUENCE: 55

Pro Leu Gly Leu Trp Ala
1               5

<210> SEQ ID NO 56
<211> LENGTH: 8
<212> TYPE: PRT
<213> ORGANISM: Artificial Sequence
<220> FEATURE:
<223> OTHER INFORMATION: chemically synthesized

<400> SEQUENCE: 56

Gly Pro Gln Gly Ile Ala Gly Gln
1               5

<210> SEQ ID NO 57
<211> LENGTH: 8
<212> TYPE: PRT
<213> ORGANISM: Artificial Sequence
<220> FEATURE:
<223> OTHER INFORMATION: chemically synthesized

<400> SEQUENCE: 57

Gly Pro Gln Gly Leu Leu Gly Ala
1               5

<210> SEQ ID NO 58
<211> LENGTH: 5
<212> TYPE: PRT
<213> ORGANISM: Artificial Sequence
<220> FEATURE:
<223> OTHER INFORMATION: chemically synthesized

<400> SEQUENCE: 58

Gly Ile Ala Gly Gln
1               5

<210> SEQ ID NO 59
<211> LENGTH: 8
<212> TYPE: PRT
<213> ORGANISM: Artificial Sequence
<220> FEATURE:
<223> OTHER INFORMATION: chemically synthesized

<400> SEQUENCE: 59

Gly Pro Leu Gly Ile Ala Gly Ile
1               5

<210> SEQ ID NO 60
<211> LENGTH: 8
<212> TYPE: PRT
<213> ORGANISM: Artificial Sequence
```

<220> FEATURE:
<223> OTHER INFORMATION: chemically synthesized

<400> SEQUENCE: 60

Gly Pro Glu Gly Leu Arg Val Gly
1               5

<210> SEQ ID NO 61
<211> LENGTH: 8
<212> TYPE: PRT
<213> ORGANISM: Artificial Sequence
<220> FEATURE:
<223> OTHER INFORMATION: chemically synthesized

<400> SEQUENCE: 61

Tyr Gly Ala Gly Leu Gly Val Val
1               5

<210> SEQ ID NO 62
<211> LENGTH: 8
<212> TYPE: PRT
<213> ORGANISM: Artificial Sequence
<220> FEATURE:
<223> OTHER INFORMATION: chemically synthesized

<400> SEQUENCE: 62

Ala Gly Leu Gly Val Val Glu Arg
1               5

<210> SEQ ID NO 63
<211> LENGTH: 8
<212> TYPE: PRT
<213> ORGANISM: Artificial Sequence
<220> FEATURE:
<223> OTHER INFORMATION: chemically synthesized

<400> SEQUENCE: 63

Ala Gly Leu Gly Ile Ser Ser Thr
1               5

<210> SEQ ID NO 64
<211> LENGTH: 8
<212> TYPE: PRT
<213> ORGANISM: Artificial Sequence
<220> FEATURE:
<223> OTHER INFORMATION: chemically synthesized

<400> SEQUENCE: 64

Glu Pro Gln Ala Leu Ala Met Ser
1               5

<210> SEQ ID NO 65
<211> LENGTH: 8
<212> TYPE: PRT
<213> ORGANISM: Artificial Sequence
<220> FEATURE:
<223> OTHER INFORMATION: chemically synthesized

<400> SEQUENCE: 65

Gln Ala Leu Ala Met Ser Ala Ile
1               5

<210> SEQ ID NO 66
<211> LENGTH: 8
<212> TYPE: PRT
<213> ORGANISM: Artificial Sequence
<220> FEATURE:

```
<223> OTHER INFORMATION: chemically synthesized

<400> SEQUENCE: 66

Ala Ala Tyr His Leu Val Ser Gln
1               5

<210> SEQ ID NO 67
<211> LENGTH: 8
<212> TYPE: PRT
<213> ORGANISM: Artificial Sequence
<220> FEATURE:
<223> OTHER INFORMATION: chemically synthesized

<400> SEQUENCE: 67

Met Asp Ala Phe Leu Glu Ser Ser
1               5

<210> SEQ ID NO 68
<211> LENGTH: 8
<212> TYPE: PRT
<213> ORGANISM: Artificial Sequence
<220> FEATURE:
<223> OTHER INFORMATION: chemically synthesized

<400> SEQUENCE: 68

Glu Ser Leu Pro Val Val Ala Val
1               5

<210> SEQ ID NO 69
<211> LENGTH: 8
<212> TYPE: PRT
<213> ORGANISM: Artificial Sequence
<220> FEATURE:
<223> OTHER INFORMATION: chemically synthesized

<400> SEQUENCE: 69

Ser Ala Pro Ala Val Glu Ser Glu
1               5

<210> SEQ ID NO 70
<211> LENGTH: 8
<212> TYPE: PRT
<213> ORGANISM: Artificial Sequence
<220> FEATURE:
<223> OTHER INFORMATION: chemically synthesized

<400> SEQUENCE: 70

Asp Val Ala Gln Phe Val Leu Thr
1               5

<210> SEQ ID NO 71
<211> LENGTH: 8
<212> TYPE: PRT
<213> ORGANISM: Artificial Sequence
<220> FEATURE:
<223> OTHER INFORMATION: chemically synthesized

<400> SEQUENCE: 71

Val Ala Gln Phe Val Leu Thr Glu
1               5

<210> SEQ ID NO 72
<211> LENGTH: 8
<212> TYPE: PRT
<213> ORGANISM: Artificial Sequence
<220> FEATURE:
<223> OTHER INFORMATION: chemically synthesized
```

<400> SEQUENCE: 72

Ala Gln Phe Val Leu Thr Glu Gly
1               5

<210> SEQ ID NO 73
<211> LENGTH: 8
<212> TYPE: PRT
<213> ORGANISM: Artificial Sequence
<220> FEATURE:
<223> OTHER INFORMATION: chemically synthesized

<400> SEQUENCE: 73

Pro Val Gln Pro Ile Gly Pro Gln
1               5

<210> SEQ ID NO 74
<211> LENGTH: 60
<212> TYPE: DNA
<213> ORGANISM: Artificial Sequence
<220> FEATURE:
<223> OTHER INFORMATION: chemically synthesized

<400> SEQUENCE: 74
cagagactga tggaggacat ctgcctgccg agatggggat gcctgtggga agacgacttc        60

<210> SEQ ID NO 75
<211> LENGTH: 39
<212> TYPE: DNA
<213> ORGANISM: Artificial Sequence
<220> FEATURE:
<223> OTHER INFORMATION: chemically synthesized

<400> SEQUENCE: 75
ggctcgagcg gtggcagcgg tggctctggt ggatccggt        39

<210> SEQ ID NO 76
<211> LENGTH: 24
<212> TYPE: DNA
<213> ORGANISM: Artificial Sequence
<220> FEATURE:
<223> OTHER INFORMATION: chemically synthesized

<400> SEQUENCE: 76
actggccgtg gtccaagctg ggtt        24

<210> SEQ ID NO 77
<211> LENGTH: 9
<212> TYPE: DNA
<213> ORGANISM: Artificial Sequence
<220> FEATURE:
<223> OTHER INFORMATION: chemically synthesized

<400> SEQUENCE: 77 ggcggtacc        9

<210> SEQ ID NO 78
<211> LENGTH: 13
<212> TYPE: PRT
<213> ORGANISM: Artificial Sequence
<220> FEATURE:
<223> OTHER INFORMATION: chemically synthesized

<400> SEQUENCE: 78

Gly Ser Ser Gly Gly Ser Gly Gly Ser Gly Gly Ser Gly
1               5                   10

```
<210> SEQ ID NO 79
<211> LENGTH: 3
<212> TYPE: PRT
<213> ORGANISM: Artificial Sequence
<220> FEATURE:
<223> OTHER INFORMATION: chemically synthesized

<400> SEQUENCE: 79

Gly Gly Thr
1

<210> SEQ ID NO 80
<211> LENGTH: 60
<212> TYPE: DNA
<213> ORGANISM: Artificial Sequence
<220> FEATURE:
<223> OTHER INFORMATION: chemically synthesized

<400> SEQUENCE: 80
atgtacagga tgcaactcct gtcttgcatt gcactaagtc ttgcacttgt cacgaattcg      60

<210> SEQ ID NO 81
<211> LENGTH: 20
<212> TYPE: PRT
<213> ORGANISM: Artificial Sequence
<220> FEATURE:
<223> OTHER INFORMATION: chemically synthesized

<400> SEQUENCE: 81

Met Tyr Arg Met Gln Leu Leu Ser Cys Ile Ala Leu Ser Leu Ala Leu
1               5                   10                  15

Val Thr Asn Ser
            20
```

What is claimed is:

1. A method of treating an EGFR-expressing cancer, the method comprising administering a therapeutically effective amount of a composition comprising an activatable antibody to a subject in need thereof, the activatable antibody comprising:

an antibody or antibody fragment (AB) that binds specifically to a target, wherein the target is an epidermal growth factor receptor (EGFR), wherein the AB comprises the six complementarity determining regions (CDRs) of cetuximab;

a cleavable linker (CL) covalently linked to the AB, wherein the CL comprises a substrate (S) for an enzyme, wherein the enzyme is urokinase plasminogen activator (uPa); and a binding partner (BP) for a non-binding steric moiety (NB), wherein the BP is an albumin-binding polypeptide comprising the amino acid sequence of SEQ ID NO: 1 and the NB comprises a serum albumin, wherein the NB is covalently linked to the CL, wherein the NB does not bind specifically to the AB; and wherein when the activatable antibody is in an uncleaved state and the NB is bound to the BP, the NB interferes with binding of the AB to the target and when the activatable antibody is in a cleaved state, the NB does not interfere with binding of the AB to the target, and the activatable antibody in the uncleaved state has the structural arrangement from N-terminus to C-terminus as follows: BP-CL-AB or AB-CL-BP.

2. The method of claim 1, wherein the protease is co-localized with the target in a tissue, and wherein the protease cleaves the CL in the activatable antibody when the activatable antibody is exposed to the protease.

3. The method of claim 1, wherein the CL comprises a first flexible portion (FP1) and a second flexible portion (FP2), wherein the activatable antibody in the uncleaved state has the structural arrangement from N-terminus to C-terminus as follows: NB-FP1-S-FP2-AB, AB-FP2-S-FP1-NB, BP-FP1-S-FP2-AB, or AB-FP2-S-FP1-BP.

4. The method of claim 3, wherein the two flexible portions of the CL need not be identical to each other.

5. The method of claim 3, wherein each of FP1 and FP2 is a peptide of about 1 to 20 amino acids in length.

6. The method of claim 3, wherein at least one of FP1 or FP2 comprises an amino acid sequence selected from the group consisting of $(GS)_n$, $(GGS)_n$, $(GSGGS)_n$ (SEQ ID NO: 5) and $(GGGS)_n$ (SEQ ID NO: 6), where n is an integer of at least one.

7. The method of claim 6, wherein at least one of FP1 or FP2 comprises an amino acid sequence selected from the group consisting of GGSG (SEQ ID NO: 7), GGSGG (SEQ ID NO: 8), GSGSG (SEQ ID NO: 9), GSGGG (SEQ ID NO: 10), GGGSG (SEQ ID NO: 11), and GSSSG (SEQ ID NO: 12).

8. The method of claim 1, wherein the CL is a polypeptide of up to 50 amino acids in length or wherein S is a polypeptide of up to 15 amino acids in length.

9. The method of claim 1, wherein the AB is an antigen binding fragment selected from the group consisting of a Fab fragment, a F(ab')$_2$ fragment.

10. The method of claim 1, wherein the NB in the uncleaved activatable antibody reduces the ability of the AB to bind the target by at least 50%, as compared to the ability of the cleaved AB to bind the target.

11. The method of claim 1, wherein the activatable antibody comprises an agent conjugated to the AB, wherein the agent is a therapeutic agent, an antineoplastic agent, or a toxin or a fragment thereof.

12. The method of claim 11, wherein the agent is an agent selected from the group consisting of: an Auristatin, Auristatin E, Monomethyl auristatin E (MMAE), Desmethyl auristatin E (DMAE), Auristatin F, Monomethyl auristatin F (MMAF), Desmethyl auristatin F (DMAF), an Auristatin amide, Auristatin tyramine, Auristatin quinoline, a Dolastatin, Dolastatin 16 DmJ, Dolastatin 16 Dpv, a Maytansinoid, DM-1, DM-4, Duocarmycin, Alpha-amanitin, an Anthracycline, Doxorubicin, Daunorubicin, a Bryostatin, Camptothecin, 7-substituted Camptothecin, 10, 11-Difluoromethylenedioxycamptothecin, a Combretastatin, Debromoaplysiatoxin, Kahalalide-F, Discodermolide, an Ecteinascidin, Acyclovir, Vira A, Symmetrel, Nystatin, Turbostatin, a Phenstatin, Hydroxyphenstatin, Spongistatin 5, Spongistatin 7, Halistatin 1, Halistatin 2, Halistatin 3, a Modified Bryostatin, a Halocomstatin, a Pyrrolobenzimidazole (PBI), Cibrostatin6, Doxaliform, Cemadotin analogue (CemCH2-SH), *Pseudomonas* toxin A (PE38), *Pseudomonas* toxin A (ZZ-PE38), ZJ-101, OSW-1, a Topoisomerase inhibitor, Hemiasterlin, Cephalotaxine, Homoharringtonine, a Pyrrolobenzodiazepine dimer (PBD), a Functionalized pyrrolobenzodiazepene, a Calicheamicin, a Podophyllotoxin, a Taxane, a *Vinca* alkaloid, Fluorescein, Fluorescein isothiocyanate (FITC), Adriamycin, Cerubidine, Bleomycin, Alkeran, Velban, Oncovin, Fluorouracil, Methotrexate, Thiotepa, Bisantrene, Novantrone, Thioguanine, Procarabizine, Cytarabine, an Aminoglycoside, Streptomycin, Neomycin, Kanamycin, Amikacin, Gentamicin, Tobramycin, Streptomycin B, Spectinomycin, Ampicillin, Sulfanilamide, Polymyxin, Chloramphenicol, $^{125}$I, $^{131}$I, $^{89}$Zr, $^{111}$In, $^{123}$I, $^{131}$I, $^{201}$Tl, $^{133}$Xe, $^{11}$C, $^{62}$Cu, $^{18}$F, $^{68}$Ga, $^{13}$N, $^{15}$O, $^{38}$K, $^{82}$Rb, $^{99}$mTc (Technetium), Barium, Gold, Platinum, Tylosine, and Spectinomycin.

13. The method of claim 11, wherein the agent is conjugated to the AB via a linker.

14. The method of claim 13, wherein the linker is a cleavable linker.

* * * * *